(12) United States Patent
Ding

(10) Patent No.: US 7,292,949 B2
(45) Date of Patent: Nov. 6, 2007

(54) METHOD AND APPARATUS FOR ESTIMATING SURFACE MOISTURE CONTENT OF WOOD CHIPS

(75) Inventor: Feng Ding, Sainte-Foy (CA)

(73) Assignee: Centre de recherche industrielle du Québec, Québec (CA)

( * ) Notice: Subject to any disclaimer, the term of this patent is extended or adjusted under 35 U.S.C. 154(b) by 0 days.

(21) Appl. No.: 10/856,883

(22) Filed: Jun. 1, 2004

(65) Prior Publication Data

US 2005/0027482 A1 Feb. 3, 2005

(30) Foreign Application Priority Data

Jun. 2, 2003 (CA) .................................. 2430737

(51) Int. Cl.
*G01N 21/00* (2006.01)
*G01N 21/88* (2006.01)
*G01J 3/00* (2006.01)
*G01J 3/46* (2006.01)

(52) U.S. Cl. .................. 702/81; 356/237.1; 356/237.2; 356/402; 356/403; 356/404; 356/405; 356/406; 356/369; 356/431; 250/559.45; 250/553.46; 250/559.42; 209/555; 428/528; 162/260; 700/230

(58) Field of Classification Search .................. 702/81; 356/237.1–237.2; 250/559.45–559.46; 209/55; 700/230
See application file for complete search history.

(56) References Cited

U.S. PATENT DOCUMENTS

| | | | |
|---|---|---|---|
| 4,755,743 A * | 7/1988 | Jakkula | 324/632 |
| 6,175,092 B1 | 1/2001 | Binette et al. | |
| 6,493,076 B1 * | 12/2002 | Laitinen | 356/237.2 |
| 6,526,119 B1 | 2/2003 | Lappalainen et al. | |
| 2004/0059694 A1 * | 3/2004 | Darken et al. | 706/21 |

OTHER PUBLICATIONS

Swedish Pulp and Paper Research Institute, Proceedings, Control System 2002, Jun. 3-5, 2002, Stckholm, Sweden.

* cited by examiner

*Primary Examiner*—Hal Wachsman
*Assistant Examiner*—Sujoy Kundu
(74) *Attorney, Agent, or Firm*—Jean-Claude Boudreau

(57) ABSTRACT

Method and apparatus for estimating surface moisture content of wood chips employing a surface moisture measurement obtained from a non-contact surface moisture sensor, which measurement is calibrated with values of a set of optical parameters, such as HSL color camera signals, representing light reflection characteristics of the wood chips in order to estimate the surface moisture content thereof.

4 Claims, 41 Drawing Sheets

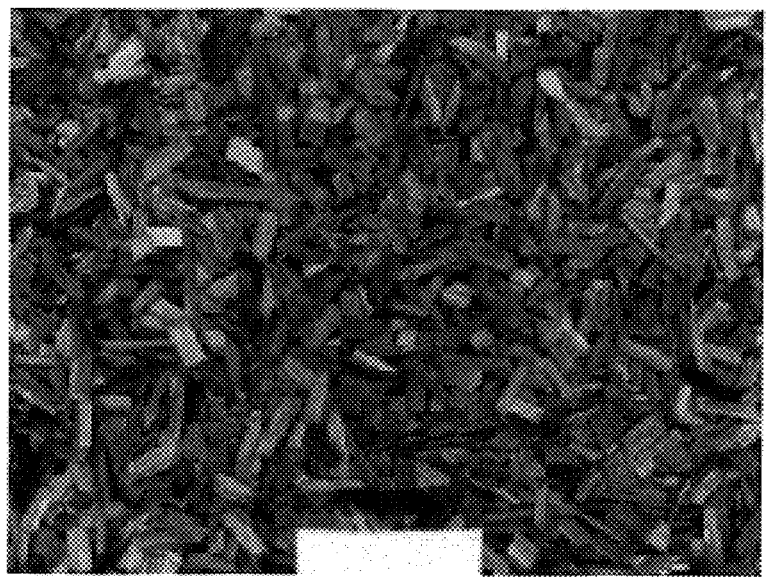
_Fig-12A_
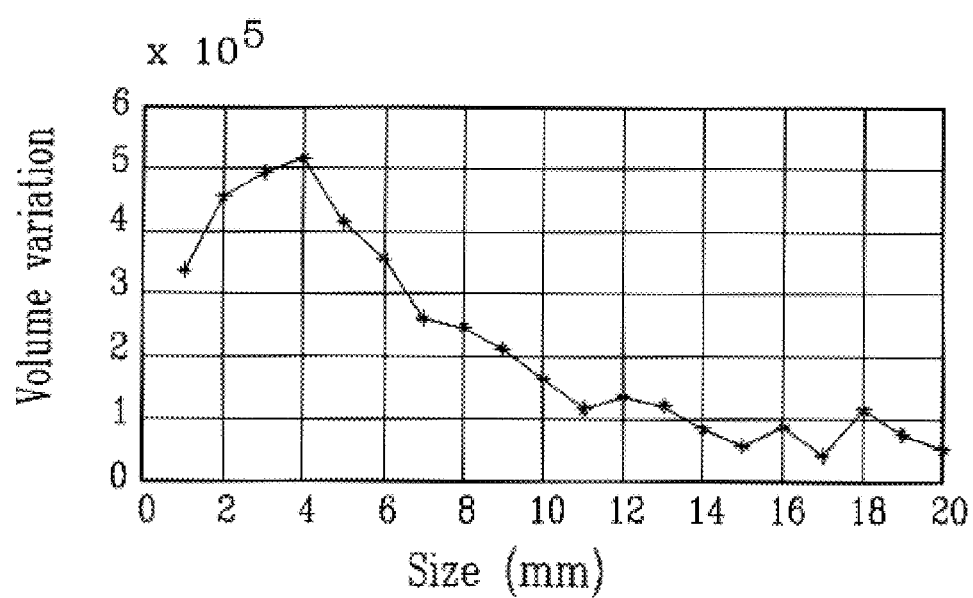
_Fig-12B_

SELECTED CLASS DATA [X]

- MEAN
  | 394.39864 | -0.7306392 | -19.254214 |

- COVARIANCE
  | 359.05931 | -122.97877 | 133.24291 |
  | -122.97877 | 855.68602 | -594.63846 |
  | 133.24291 | -594.63846 | 1438.1686 |

SCALE FACTOR: 3

[ CANCEL ] [ OK ]

Fig-26A

SELECTED CLASS DATA [X]

- MEAN
  | 731.36930 | 19.976359 | 233.01368 |

- COVARIANCE
  | 5437.9639 | -432.88308 | 596.19948 |
  | -432.88308 | 649.20312 | 565.56297 |
  | 596.19948 | 565.56297 | 2902.3525 |

SCALE FACTOR: 0.5

[ CANCEL ] [ OK ]

Fig-26B

SELECTED CLASS DATA [X]

- MEAN
  | 415.95863 | 44.710763 | 126.88453 |

- COVARIANCE
  | 7275.9915 | 212.10041 | 3755.3161 |
  | 212.10041 | 1427.3523 | 233.11694 |
  | 3755.3161 | 233.11694 | 5820.5484 |

SCALE FACTOR: 0.5

[ CANCEL ] [ OK ]

Fig-26C

Sound Birch

Sound Birch

Birch with bark

Birch with bark

Birch with knots

Birch with knots

Sound Spruce

Sound Spruce

Spruce with bark

Spruce with bark

Spruce with knots

Spruce with knots

Spruce with rot

Spruce with rot

METHOD AND APPARATUS FOR ESTIMATING SURFACE MOISTURE CONTENT OF WOOD CHIPS

BACKGROUND OF INVENTION

In the past years, significant efforts have been devoted to develop processes for the production of pulp and paper products aimed at reducing manufacturing costs while improving product quality. Quality control of the raw materials entering in the production of pulp and paper products using either chemical or thermo mechanical pulping (TMP) processes, particularly regarding wood chips used, has been identified as a key factor in process optimization. The bleaching agent (ex. hydrosulphite, peroxide) is widely used to improve pulp brightness to a specified level which fulfills customers needs. Especially for TMP, the objective of process control is to have stable, high pulp quality with minimal energy and bleaching agent consumption. Thus, a constant flow of chips into the refiners is an important parameter for maintaining good refining performance. As a raw material, wood chips are heterogeneous and when fed into a refiner can vary in terms of wood chip species, chip size distribution, moisture content, bulk and basic density, freshness and impurities content (bark, knot, rot, etc.). These variations disturb in turn TMP process control and influence pulp quality, as mentioned by Smook, G. A. in "Handbook for Pulp & Paper Technologies", Joint Texbook Committee of the Paper Industry, 54, (1982), as well as by Wood, J. R. in "Chip Quality Effects in Mechanical Pulping—a Selected Review", *TAPPI Pulping Conference*, Proceedings, 491-497 (1996). More specifically, the variations in the wood raw materials and its fibers may give rise to 30-40% of variations in the pulp properties as taught by Lundgwist, S. O., et al, in "Wood Fiber Simulation—A Model Based Tool for Optimized Wood and Fiber Utilization", Control System 2002, Proceedings, June 3-5, Stockholm, Sweden, 164-169 (2002).

In mills, visual evaluation of wood chip quality is widely used. From the chip color, a specialist can determine the chip species and estimate freshness, bark, rot, and knot contents. A known approach consists of sorting trees according to their species or blend of species prior to wood chips manufacturing, to produce corresponding batches of wood chips presenting desired characteristics associated with these species. Typically, hardwood trees such as poplar, birch and maple are known to generally produce pale wood chips while conifers such as pine, fir and spruce are known to generally yield darker wood chips. In practice, wood chips batches can either be produced from trees of a same species or from a blend of wood chips made from trees of plural species, preferably of a common category, i.e., hardwood trees or conifers, to seek wood chips uniformity. However, chips characteristics basically depending on initial bark content of wood chips used, the mere knowledge of wood chips species composition for a given batch does not necessarily give a reliable indication of the chips quality.

Many studies have shown that wood species is the dominant factor in pulping performance and pulp quality. The spruce family is the most favourable species for TMP as mentioned by Varhimo, A. et al, in "Raw Materials" in Sundbolm, J. "Mechanical Pulping" Chapter 5, Fapet OY, 66-104 (1999). Homogeneity and low fines content of chip size distribution produce good pulp strength, while knot and bark contents decrease the strength and brightness of the pulp as mentioned by Brill, J. W. in "Effects of Wood and Chip Quality on TMP Properties". International Mechanical Pulping Conference, Proceedings, Stockholm 153-162 (1985). Continuous variations in wood basic density and moisture content occurring in chip flow tend to cause variations in refining consistency, which in turn affect pulp uniformity and energy consumption as mentioned by Trväinen, J. in "The influence of Wood Properties on the Quality of TMP Made From Norway Spruce (Picea abies)—Wood From Old growth Forests, First-thinning, and Sawmill Chips," International Mechanical Pulping Conference, Proceedings, 23-34 (1995). Rot should be avoided as it impairs the brightness and strength properties of paper as discussed by Hartler, N. in "Wood Quality Requirements in Mechanical Pulping", Nordic Pulp and Paper Research Journal. (1): 4 (1986). Knots produce low strength pulp and are predominant among oversize chips. They also reduce pulp brightness as mentioned by Brill and Wood in the above cited papers. Fresh wood chips increase productivity, decrease hydrosulfite consumption, and stabilize the pulping process as mentioned by Ding, F. et al, in "Economizing the Bleaching Agent Consumption by Controlling Wood Chip Brightness", Control System 2002, Proceedings, June 3-5, Stockholm, Sweden, 205-209 (2002). A quantitative evaluation of pulpwood chip quality has been proposed for the chemical pulping process by Hatton, J. V. in "Chip Quality Monograph", Joint Textbook Committee of the Paper Industry. 311 (1999). However, this evaluation being wholly based on offline laboratory measurements, accuracy depends on sampling method, frequency, and quantities. Because offline measurements cannot be used to stabilize, predict, and optimize processes, this evaluation can seldom be used in the industry. An online approach to control quality of wood chips employed in the wood chips manufacturing method disclosed in U.S. Pat. No. 5,577,671 issued on Nov. 26, 1996 to Seppanen, which method consists of separating from ground whole-tree chips, bark and cellulose wood chips through a series of separation stages including pneumatic separation, vibration segregation with sieve and color difference sorting. The resulting low bark, pale wood chips can be then processed using a minimum quantity of bleaching agent. Although processing cost can be minimized accordingly, added manufacturing cost due to bark separation step may still maintain overall production cost at a high level.

An improved online technology is discussed in U.S. Pat. No. 6,398,914 B1 issued to the present assignee, which discloses a method and apparatus for classifying batches of wood chips according to light reflection characteristics to allow optimal use of dark wood chips in pulp an paper processes. Chip brightness is a characteristic related to chip freshness, a very important parameter for TMP process, which presents the chip aging state. Chip aging is a very complex phenomenon that depends on the wood species, log and chip storage, and ambient air condition. It is very difficult and unnecessary to estimate effective chip age from its actual aging state. Although chip aging can be observed from chip brightness, it is only useful for substantially unvaried wood species. When an unknown proportion of wood species is present, more information is needed to provide reliable chip quality assessment.

The importance of chip quality for pulp and paper production processes, and especially for the TMP process has long been recognized, but heretofore, no multi-variable, reliable method for estimating the quality of wood chips has been proposed using known offline or online measurement technologies.

SUMMARY OF INVENTION

It is a main object of the present invention to provide a method for estimating surface moisture content of wood chips for use in a pulp and paper production process.

The proposed method may be advantageously used to assist pulp and paper mill operators to pay chip suppliers a reasonable price and to better manage the chip yard, to serve as a basis for predictive and optimal refining control, as well as for predicting pulp and paper quality for a given pulp and paper manufacturing process.

According to the above main object, from a broad aspect of the present invention, there is provided a method for estimating surface moisture content of wood chips comprising:

i) obtaining a chip surface moisture measurement from a non-contact surface moisture sensor; and ii) calibrating said surface moisture measurement with values of a set of optical parameters representing light reflection characteristics of said wood chips, to estimate said surface moisture content.

There is also provided an apparatus for estimating surface moisture content of wood chips comprising a non-contact surface moisture sensor for generating a chip surface moisture measurement, image creating means for generating values of a set of optical parameters representing light reflection characteristics of said wood chips, and data processor means for calibrating said surface moisture measurement with said parameters values to estimate said surface moisture content.

BRIEF DESCRIPTION OF THE DRAWINGS

Preferred embodiments of the present invention will now be described in detail with reference to the accompanying drawings in which:

FIGS. 11a-15a show images of wood chips sub-samples that were obtained through successive sifting steps to group wood chips according to complementary ranges of sizes;

FIGS. 11b-15b are graphs corresponding to FIGS. 11a-15a, showing the behavior of volume variation as the size of wood chips increases;

FIGS. 26a-26c are computer-generated screens presenting the basic statistical parameters (mean values, covariance values, scale factor) for a basic class structure consists of three basic color classes;

FIGS. 29a to 35a show a series of exemplary raw images to be classified;

FIGS. 29b to 35b show corresponding classified images wherein the detected impurities are represented in contrast;

DETAILED DESCRIPTION OF THE PREFERRED EMBODIMENTS

Figure 1:
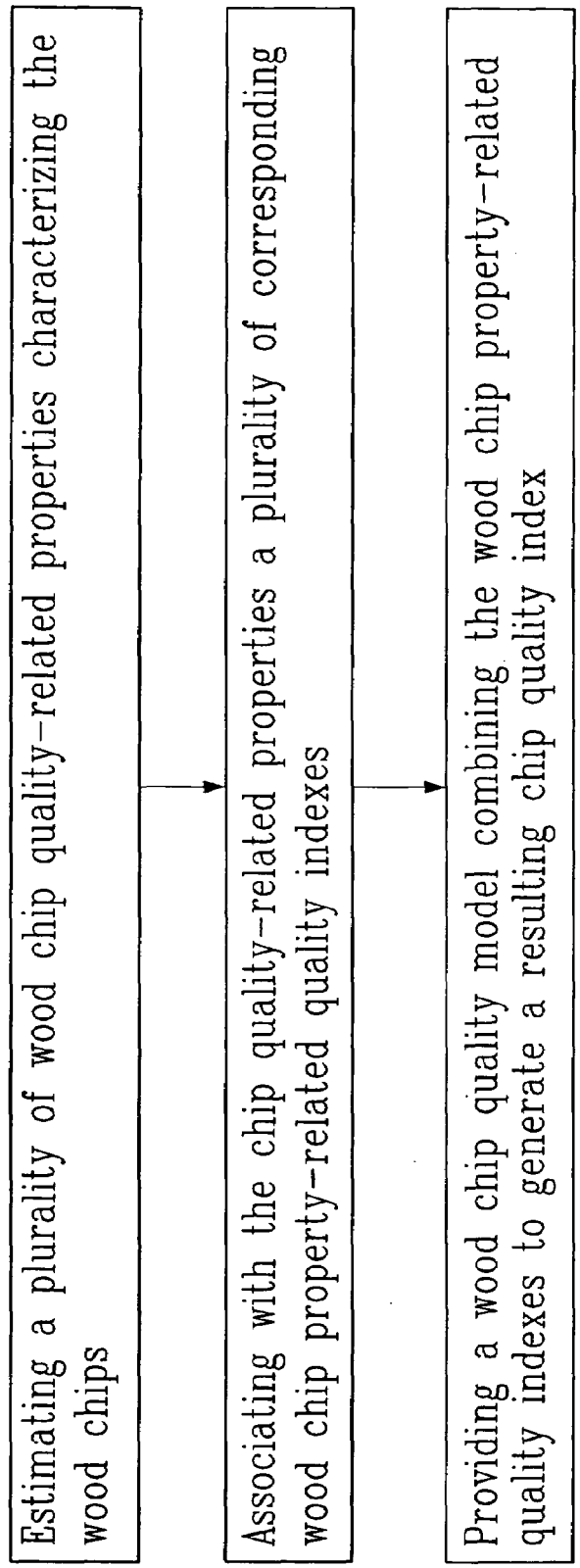
FIG. 1 is a process flow diagram representing the main steps of the basic quality estimating method of the present invention.

For pulp and paper production using chemical or TMP process, online chip quality measurement is desirable because chip quality influences not only pulp and paper quality but also process control. According to the present invention, chip quality is defined and modelled mainly on the basis of online measurements of chip properties that can be used to pay chip suppliers, manage chip yards, monitor chip feeding, and achieve predictive and optimal refining control. Depending upon the selected chip properties, the proposed quality estimating method can be used in a broad range of applications.

In a typical mill, a quality standard defined by specific property ranges is usually used at chip reception such as presented in Table 1:

TABLE

| Properties | | Min. | Max | Properties | Min. | Max. |
|---|---|---|---|---|---|---|
| Size mm | >28.6 | 0 | 15% | Bark | 0 | 1% |
| | 15.9-22.2 | 50% | 100% | Moisture | 25% | High |
| | 9.5-15.9 | 0 | 25% | Rot | 0 | 1.8% |
| | 4.8-9.5 | 0 | 15% | Freshness | | Fresh |
| | <4.8 | 0 | 1% | . | . | . |
| | Jack Pine Proportion | 0 | 10% | . | . | . |

These physical properties are normally considered as representing the quality of chips and are usually estimated by laboratory offline measurements only. Unfortunately, such offline approach cannot be used to stabilize and control a process such as TMP due to constraints of sampling size, frequency, and time delay. For this reason, a definition mainly based on online measurements is desirable.

According to the chip quality estimating method of the invention, a plurality of wood chip quality-related properties characterizing the wood chips are estimated, and a plurality of corresponding wood chip property-related quality indexes are associated with the selected properties. Hence, a wood chip quality model combining these property-related quality indexes is provided to generate a resulting chip quality index. Such model can be defined by:

$$Q = \sum_{i=1,n} b_i P_i \quad (1)$$

with:

$$\sum_{i=1,n} b_i = 1 \quad (2)$$

wherein:
Q represents the resulting chip quality index;
n represents the number of said properties;
$P_i$ represents a property of indicia i; and
$b_i$ represents a weighting factor for the property of indicia i.

The weighting factors represent the importance of related chip properties in the pulping process, which depends on the mill chip yard management, type of refiner, pulp and paper grade. The proposed model definition is flexible, with the development of measurement technologies. On the basis of such general definition, wood chip quality modeling can achieved according to the specific requirements of the application considered. Depending on pulp quality, refining requirements, and the experiences of a given mill, as exemplified in Table 1 above, some criteria have been set for chip properties. If the measured chip properties do not satisfy these criteria, the chips will be rejected so as to maintain process control, and therefore such category of chip does not need to be classified. Conveniently, chips that satisfy the criteria may be classified according to 10 different grades. As grades increase from 1 to 10, chip quality decreases accordingly. As mentioned in the quality definition, the final chip quality is based on the qualitative grade of each property in order to perform the proposed qualitative grade modeling.

The selection of the relevant properties for a specific application may be achieved considering many chip-related properties such as species composition (pure species, blend of species), chip size distribution, impurity content (bark, knot, rot), chip freshness, moisture content, density, etc. For applications involving typical TMP processes, it has be found a basic set of chip-characterizing properties include wood species composition and size distribution. In order to provide an improved quality estimation, one or more additional properties may be considered in the model, namely: impurity content and particularly bark content, freshness and moisture content. In such case, the generic model expressed by relation (1) can be expressed as follows:

$$Q = b_1 S + b_2 Z + b_3 B + b_4 F + b_5 M \quad (3)$$

wherein:
Q represents the resulting chip quality index;
S represents wood species composition;
Z represents chip size distribution;
B represents bark content;
F represents chip freshness;
M represents moisture content; and
$b_1$-$b_5$ represent weighting factors associated with the above properties.

A detailed description of the quality estimation method is presented below with reference to exemplary experiments designed to be representative of typical wood chip species composition used as raw materials for a typical TMP process. Two sets of trials were designed and performed, involving sampled pure species that were combined to form several test samples whose compositions are shown in Table 2.

TABLE 2

| No | Black Spruce | Balsam Fir | Jack Pine | White Birch |
|---|---|---|---|---|
| | Extreme vertex design | | | |
| 1 | 0 | 20% | 40% | 40% |
| 2 | 100% | 0 | 0 | 0 |
| 3 | 0 | 100% | 0 | 0 |
| 4 | 60% | 0 | 0 | 40% |
| 5 | 0 | 60% | 40% | 0 |
| 6 | 60% | 0 | 40% | 0 |
| 7 | 0 | 60% | 0 | 40% |
| 8 | 20% | 0 | 40% | 40% |
| | Two replicated points | | | |
| 9 | 100% | 0 | 0 | 0 |
| 10 | 0 | 100% | 0 | 0 |
| | Two reference points | | | |
| 11 | 0 | 0 | 100% | 0 |
| 12 | 0 | 0 | 0 | 100% |

Figure 2:
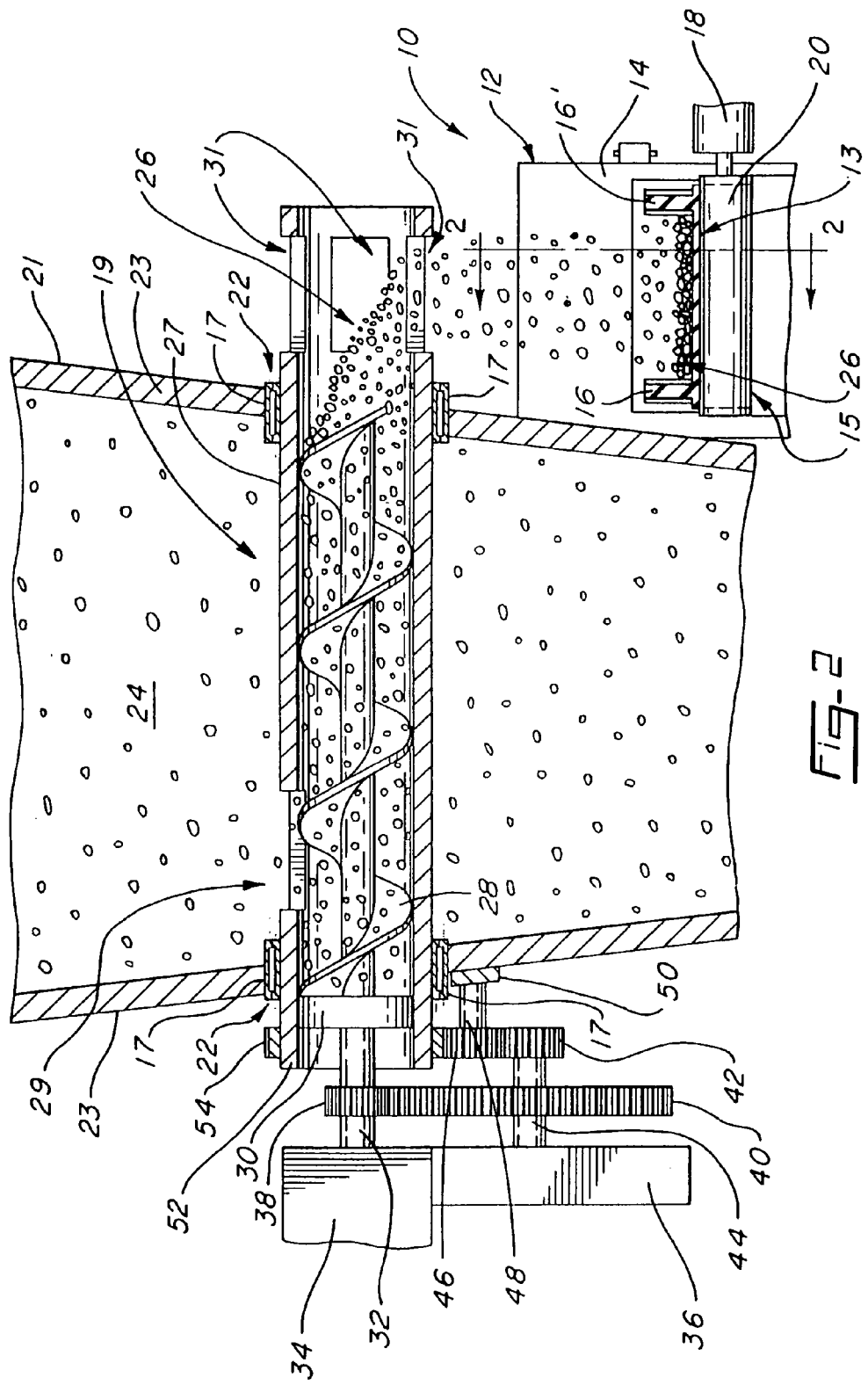
FIG. 2 is a partially cross-sectional end view of a receiving hopper provided with a sampling screw feeding a conveyor transporting wood chips through an optical inspection station that can be used to perform the chip quality estimating method of the invention.

The first set of trials involving 8 test samples was considered as part as a first order, extreme vertex experimental plan. Black spruce and balsam fir, two species widely used in TMP, and jack pine and white birch, species that are expected to be used in the future, were chosen. After registering the pure chip species and its initial age, the pure chip species were outdoors separately during autumn, winter, and spring. Five groups of chip samples were constituted at a sampling frequency of about 3 weeks, designated by A, B, C, D, E, and F test groups. Since the time interval between groups D and E was during the winter, chip ageing had stopped, and consequently, no test was performed during this period. The purpose of such first set of trials was to assess the effects of mixtures of the four species and their ageing on final pulp and paper properties. In the second set of trails, the two main species, namely, black spruce and balsam fir, were used as replication points 8, 9 in Table 2. The wood chips came directly from the sawmill and there ages were unknown. The freshest chips available were chosen. The main variables considered in the plan were: basic density, size distribution, and moisture content. A regular full factorial design was used for these three variables. The same high density species as those included in the first set were used. Thus, the second set of tests could also serve to check the results of the first set. These tests were performed in the summer, and the results were used to study fast chip-ageing conditions. Chip physical properties were measured before refining using offline laboratory and online methods. The offline measurements followed PAPTAC standard methods from experimental pulping results obtained with a Metso CD-300 TMP pilot plant. Before entering the plant, the chips were washed. The refining process was divided into two stages: the first stage was performed at 128° C. and the second stage was atmospheric refining. Four freeness/energy levels were obtained by adjusting the plate gap during the second stage. Following PAPTAC standard methods, a full evaluation of pulp and paper properties was performed. The online measurements were carried out using a wood chip optical inspection apparatus known as CMS-100 chip management system commercially available from the Assignee Centre de Recherche Industrielle du Quebec (Ste-Foy, Quebec, Canada), which measured a number of optical properties and moisture content. Such wood chip inspection apparatus is described in U.S. Pat. No. 6,175,092 B1 issued on Jan. 16, 2001 to the present assignee, and will be now described in more detail in the context of the chip quality estimation method of the present invention Referring now to FIG. 2, a chip optical inspection apparatus that can be used for performing optical parameters measurements for used with the proposed quality estimation method will now be described. Such optical inspection apparatus is capable of generating color image pixel data through an optical inspection technique whereby polychromatic light is directed onto an inspected area of the wood chips, followed by sensing light reflected from the inspected area to generate the color image pixel data representing values of color components within one or more color spaces (RGB, HSL) for pixels forming an image of the inspected area. The optical inspection apparatus generally designated at 10 includes an inspection station 12 comprising an enclosure 14 through which extends a powered conveyor 15 coupled to a drive motor 18. The conveyor 15 is preferably of a trough type having a belt 13 defining a pair of opposed lateral extensible guards 16, 16' of a known design, for keeping the material to be inspected on the conveyor 15. Adjacent an input end 29 of the conveyor 15 is an hopper 21 for receiving at an upper inlet thereof (not shown) a batch 24 of wood chips to be inspected. It is to be understood that the quality of other similar wooden materials for use as raw material for a particular pulp and paper process could be advantageously estimated in accordance with the present invention, such as flakes, shavings, slivers, splinters and shredded wood. Typically, the wood chips 26 may be caused to flow under gravity and discharged through a controlled outlet (not shown) provided at the bottom part of the upper 21 for further processing. Radially extending through a pair of opposed openings 22 receiving rotary bearings 17 provided on the peripheral wall 23 of the hopper 21 is a sampling device 19 having an elongated cylindrical sleeve 27 of a circular cross-section adapted to receive for rotation therein a feeding screw 28 of a known construction. The sleeve 27 has a lateral input opening 29 allowing wood chips 26 to cyclically reach an input portion of the screw 28 whenever the sleeve opening 29 passes through an upper position as shown in FIG. 1. The sleeve 27 further has one or more output openings 31 generally disposed over the conveyer input end 29 to allow substantially uniform discharge of the sampled wood chips 26 on the conveyer belt 13. The feeding screw 28 has a base disk 30 being coupled to the driven end of a driving shaft 32 extending from a drive motor 34 mounted on a support frame 36, which motor 34 imparts rotation to the screw 28 at a given RPM. The driving shaft 32 is provided with a small driving gear 38 cooperating with a large gear 40 and a small gear 42 mounted on first idle shaft 44 supported by base 36, to transmit driving couple at a lower RPM to a reversing gear 46 mounted on a second idle shaft 48 rotatably engaging a support member 50 rigidly secured to the outer surface of hopper 21. The sleeve 27 has a driven end 52 provided with an outer annular disk 54 having radially extending gear teeth cooperating with the reversing gear 46 to impart rotation to the sleeve in a direction opposed to clockwise rotation of screw 28 and at a lower RPM, as will be explained later in more detail.

Figure 3:
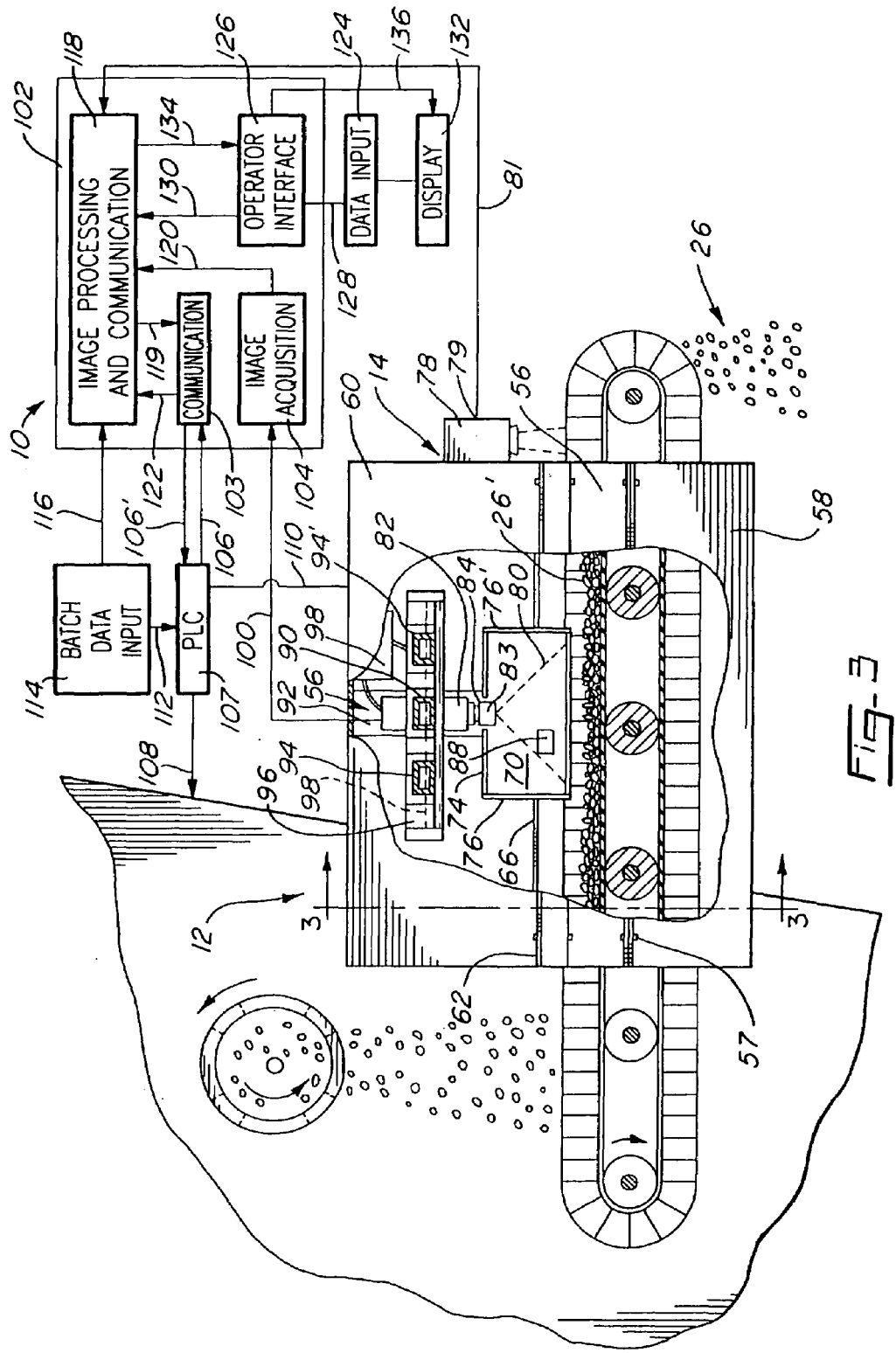
FIG. 3 is a partially cross-sectional side view along section line 2-2 of the inspection station shown in FIG. 1 and being connected with a computer unit shown in block diagram.
Figure 4:
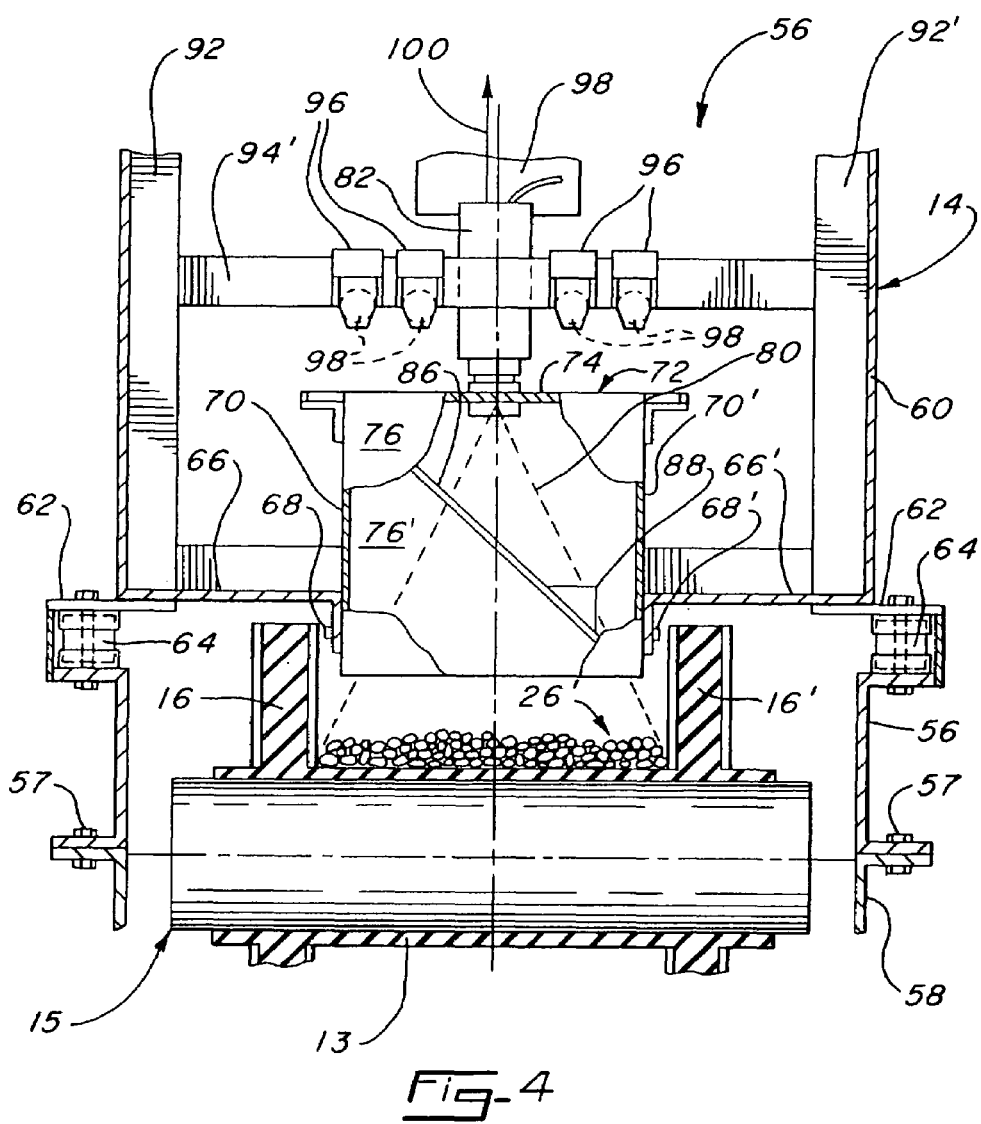
FIG. 4 is a partial cross-sectional end view along section line 3-3 of FIG. 2, showing the internal components of the inspecting station.

Turning now to FIGS. 3 and 4, internal components of the inspection station 12 will be now described. The enclosure 14 is formed of a lower part 56 for containing the conveyor 15 and being rigidly secured to a base 58 with bolt assemblies 57, and an upper part 60 for containing the optical components of the station 12 and being removably disposed on supporting flanges 62 rigidly secured to upper edge of the lower part 56 with bolted profile assemblies 64. At the folded ends of a pair of opposed inwardly extending flanged portions 66 and 66' of the upper part are secured through bolts 68 and 68' side walls 70 and 70' of a shield 72 further having top 74, front wall 76 and rear wall 76' to optically isolate the field of view 80 of a camera 82 for optically covering superficial wood chips 26' included in a representative portion of the inspected wood chips batch and being disposed within an inspection area. The camera 82 is located over the shield 72 and has an objective downwardly extending through an opening 84 provided on the shield top 74, as better shown in FIG. 3. Preferably, the distance separating camera objective 83 and superficial wood chips 26' is kept substantially constant by controlling the input flow of matter, in order to prevent scale variations that could adversely affect the optical properties measurements. Otherwise, the camera 82 may be provided with an auto-focus device as known in the art, preferably provided with distance measuring feature to normalize the captured image data considering the variation of the inspected area. The apparatus 10 may be also provided with air condition sensors for measuring air temperature, velocity, relative humidity, which measurement may be used to stabilize operation of the inspection station, and to derive estimate average moisture content, as will be explained later in more detail. Superficial wood chips 26' are distributed onto the conveyor belt 13 to present light reflection characteristics which are substantially representative of the wood chips 26 of the inspected batch. The camera 82 is used to sense light reflected on superficial wood chips 26' to produce electrical signals representing reflection intensity values for the superficial wood chips 26'. A color RGB CCD video camera such as Hitachi model no. HVC20 is used to generate the color pixel data as main optical properties considered by the quality estimation method of the invention. Diagonally disposed within shield 72 is a transparent glass sheet acting as a support for a calibrating reference support 88 as better shown in FIG. 4, whose function will be explained later in more detail. As shown in FIG. 3, the camera 82 is secured according to an appropriate vertical alignment on a central transverse member 90 supported at opposed end thereof to a pair of opposed vertical frame members 92 and 92' secured at lower ends thereof on flanged portions 66 and 66' as shown in FIG. 4. Also supported on the vertical frame members 92 and 92' are front and rear transverse members 94 and 94'. Transverse members 90, 94 and 94' are adapted to receive elongate electrical light units 96 which use standard fluorescent tubes 98 in the example shown, to direct light substantially evenly onto the inspected batch portion of superficial wood chips 26'. The camera 82 and light units 96 are powered via a dual output electrical power supply unit 98. Electrical image signal is generated by the camera 82 through output line 100. The camera 82 is used to sense light reflected on superficial chips 26' to generate color image pixel data representing values of color components within a RGB color space, for pixels forming an image of the inspected area, which color components are preferably transformed into additional color components within further standard color spaces, namely LHS to provide complementary optical parameters, and LAB color space for impurities classification purpose as will be explained later in more detail. When used in cold environment, the enclosure 14 is preferably provided with a heating unit (not shown) to maintain the inner temperature at a level ensuring normal operation of the camera 82.

Referring to FIG. 3, a moisture sensing unit 78 is shown which is preferably disposed near the inspection station 12. The sensing unit 78 is used measure variations in the chip surface moisture content, either between the batches or within any specific batch. A will be explained later in detail, the chip moisture content that can be derived from such measurement is an important property to be considered in many application of the chip quality estimation method of the present invention. Moreover, chip surface moisture variations affect reflectance characteristics of the superficial wood chips 26', thereby affecting reflection intensity values as measured by the camera 82. While batches of wood chips stored in large containers before processing generally exhibit substantially uniform and stable moisture contents, chips batches stored in open sites may present moisture variations which may have a material effect on the reflectance measurements. The moisture sensing unit 78 is preferably a non-contact sensing device such as the near-infrared sensor MM710 supplied by NDC Infrared Engineering, Irwindale Calif. The unit 78 generates at an output 79 thereof electrical signals representing mean surface moisture values for the superficial wood chips 26'.

Figure 5:
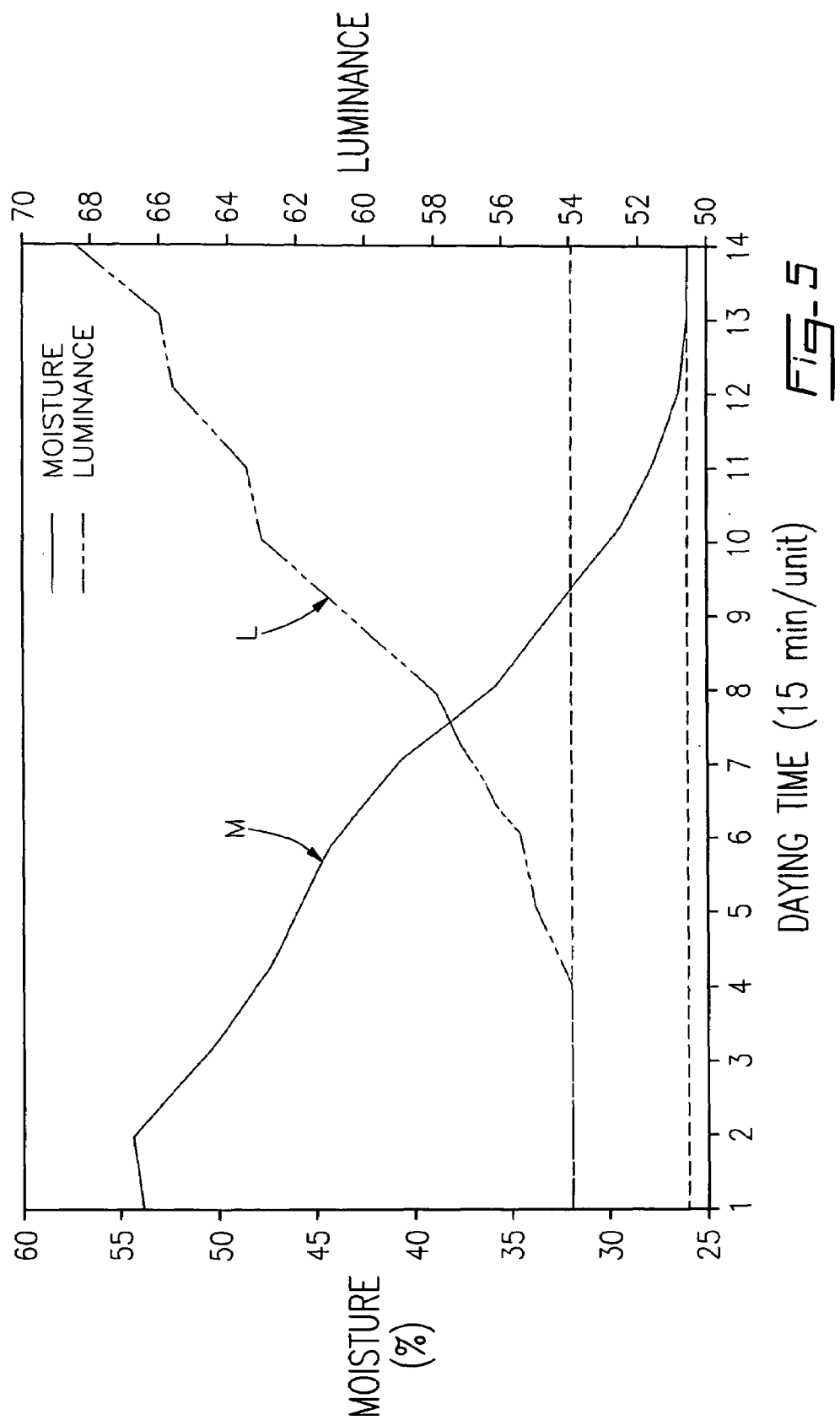
FIG. 5 is a graph showing the inverse relationship between moisture level and luminance level as measured on a sample of wood chips in term of drying time.

Referring to FIG. 5, the overall inverse relationship between surface moisture level in percentage and luminance as periodically measured during drying of a sample of wood chips is illustrated, which relation may be roughly expressed by $\Delta l \approx -k\Delta m$, wherein $\Delta m$ represents any deviation in moisture value, $\Delta l$ represents a corresponding variation in luminance value, k being a scale constant having a positive real value. It can be seen that chips showing an initial surface moisture content of 54% as shown by curve M intersecting the left vertical axis, are roughly 27% brighter (passing from 54 to 68.5 in luminance as shown by curve L intersecting the right vertical axis) after their moisture was reduced to 26% after drying. That shift in measured luminance may be compensated by normalizing the reflection intensity values according to corresponding surface moisture deviations from a predetermined reference moisture value, as will be later explained in more detail.

Control and processing elements of the apparatus 10 will be now described with reference to FIG. 3. The apparatus 10 further comprises a computer unit 102 used as a data processor, which has an image acquisition module 104 coupled to line 100 for receiving color image pixel signals from camera 82, which module 104 could be any image data acquisition electronic board having capability to receive and process standard image signals such as model Meteor-2™ from Matrox Electronic Systems Ltd (Canada) or an other equivalent image data acquisition board currently available in the marketplace. The computer 102 is provided with an external communication unit 103 being coupled for bi-directional communication through lines 106 and 106' to a conventional programmable logic controller (PLC) 107 for controlling operation of the sample screw drive 28 and conveyor drive 18 through lines 108 and 110 respectively according to a predetermined program. The PLC 107 receives from line 112 batch data entered via an input device 114 by an operator in charge of batch registration and dumping operations, as will be explained later in more detail. The input device 114 is connected through a further line 116 to an image processing and communication software module 118 outputting control data for PLC through line 119 while receiving acquired image data and PLC data through lines 120 and 122, respectively. The image processing and communication module 118 receives input data from a computer data input device 124, such as a computer keyboard, through an operator interface software module 126 and lines 128 and 130, while generating image output data toward a display device 132 through operator interface module 126 and lines 134 and 136. Module 118 also receives the moisture indicating electrical signals through a line 81.

Figure 6:
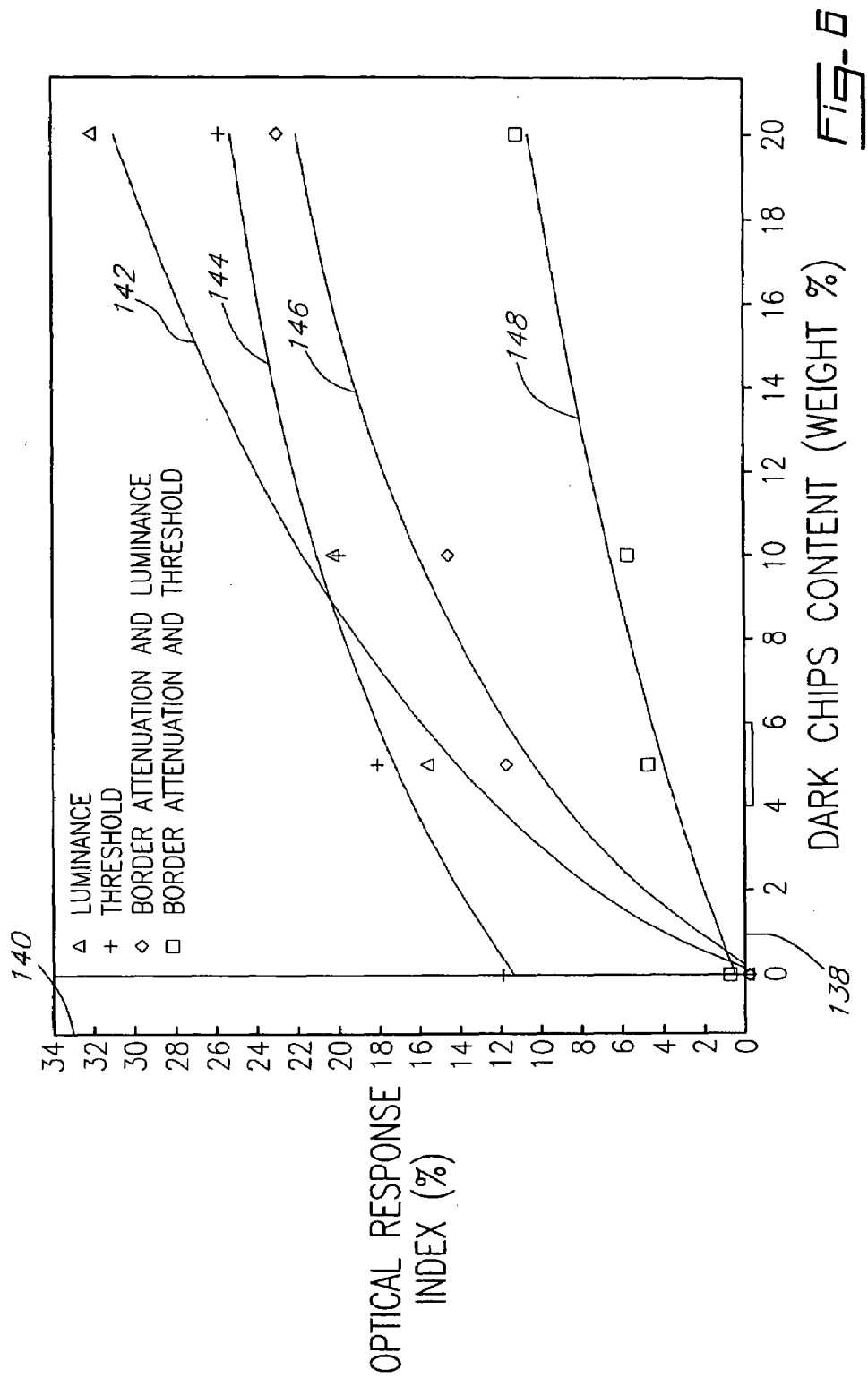
FIG. 6 is a graph showing a set of curves representing general relations between measured optical characteristics and dark wood chips contain associated with several samples.

Turning now to FIG. 6, general relations between measured optical characteristics and dark wood chips content associated with several samples are illustrated by the curves traced on the graph shown, whose first axis 138 represents dark chips content by weight percentage characterizing the sample, and whose second axis 140 represents corresponding optical response index measured. In the example shown, four curves 142, 144, 146, and 148 have been fitted on the basis of average optical response measurements for four (4) groups of wood chips samples prepared to respectively present four (4) distinct dark chips contents by weight percentage, namely 0% (reference group), 5%, 10% and 20%. Measurements were made using a RGB color camera coupled to an image acquisition module connected with a computer, as described before. To obtain curves 142 and 146, luminance signal values derived from the RGB signals corresponding to all considered pixels were used to derive an optical response index which is indicative of the relative optical reflection characteristic of each sample. As to curve 142, mean optical response index was obtained according to the following ratio:

$$I = \frac{L_R}{L_S} - 1 \qquad (4)$$

Wherein I is the optical response index, $L_R$ is a mean luminance value associated with the reference samples and $L_S$ is a mean luminance value based on all considered pixels associated with a given sample. Curve 146 was obtained through computer image processing to attenuate chip border shaded area which may not be representative of actual optical characteristics of the whole chip surface. To obtain curves 144 and 148, reflection intensity of red component of RGB signal was compared to a predetermined threshold to derive a chip darkness index according the following relation:

$$D = \frac{P_D}{P_T} \quad (5)$$

Wherein D is the chip darkness index, $P_D$ is the number of pixels whose associated red component intensity is found to be lower than the predetermined threshold ratio (therefore indicating a dark pixel) and $P_T$ is the total number of pixels considered. As for curve 146, curve 148 was obtained through computer image processing to attenuate chip border shaded areas. It can be seen from all curves 142, 144, 146, and 148 that the chip darkness index grows as dark chip content increases. Although curve 148 shows the best linear relationship, experience has shown that all of the above described calculation methods for the optical response index can be applied, provided reference reflection intensity data are properly determined, as will be explained later in more detail.

Returning now to FIGS. 2, 3 and 6, a preferred operation mode of the chip optical properties inspecting function of apparatus 10 will be now explained. An additional function related to impurities detection and classification will be explained later in detail. Referring to FIG. 3, before starting operation, the apparatus 10 must be initialized through the operator interface module 126 by firstly setting system configuration. Camera related parameters can be then set through the image processing and communication module 118, according to the camera specifications. The initialization is completed by camera and image processing calibration through the operator interface module 126.

System configuration provides initialization of parameters such as data storage allocation, image data rates, communication between computer unit 102 and PLC 107, data file management, wood species identification if known and corresponding reference threshold levels setting. As to data storage allocation, images and related data can be selectively stored on a local memory support or any shared memory device available on a network to which the computer unit 102 is connected. Directory structure is provided for software modules, system status message file, current accepted batch data, current rejected batch data and recorded rejected batch data. Image rate data configuration allows to select total number of acquired images for each batch, number of images to be stored amongst the acquired images and acquisition rate, i.e. period of time between acquisition of two successive images which is typically of about 5 sec. for a conveying velocity of about 10 feet/min. Therefore, to limit computer memory requirements, while a high number of images can be acquired for statistical purposes, only a part of these images, particularly regarding rejected batches, need to be stored. The PLC configuration relates to parameters governing communication between computer unit 102 and PLC 107, such as master-slave protocol setting (ex. DDE), memory addresses for: a) batch data input synchronization for batch presence checking following dumping information; b) alarm set for indicating a rejected batch; and c) <<heart beat>> for indication of system interruption, <<heart beat>> rate and batch presence monitoring rate. Data file management configuration relates to parameters regarding batch input data, statistical data for inspected batches, data keeping period before deletion for acceptable batch and data keeping checking rate. Statistical data file can typically contain information relating to batch number, supplier contract number, wood species, mean intensity values for Red, Green and Blue (RGB) signals, mean luminance L as well as corresponding mean H (hue) and mean S (saturation), darkness index D, date of acquisition, batch status (acceptable or rejected). Data being systematically updated on a cumulative basis, the statistical data file can be either deleted or recorded as desired by the operator to allow acquisition of new data. All predetermined desired wood species or blend thereof can be identified as well as associated reference threshold levels used as reference reflectance intensity data. For a given wood species, based on initial visual inspection by the operator of optical characteristics presented by several representative samples for that particular wood species, the operator sets a low threshold value under which an inspected batch shall be rejected as containing an unacceptable amount of dark chips for that wood species. It is to be understood that batch containing chips blend of known wood species can be characterized in a same way. In addition to visual inspection, process parameters such as required quantity of bleaching agent, processing time or spent energy measured for prior inspected batches can be recorded to find out low threshold value associated with minimum processing yield required to qualify a batch acceptable. Optionally, reference reflection intensity data may include range threshold data delimiting a plurality of wood chips quality grades regarding optical properties only. In that case, the operator may also set a maximum threshold value above which an inspected batch could be considered more than acceptable for that particular grade, ex. grade 1, and therefore could be classified in a higher quality grade of wood chips, ex. grade 2. The current levels setting for a current batch can be modified, stored or deleted as desired by the operator. It is to be understood that specific values given to the classification thresholds are also dependent upon calibration performed. Once the camera 82 is being configured as specified, calibration of the camera and the image processing module can be carried out by the operator through the operator interface, to ensure substantially stable light reflection intensities measurements as a function of time even with undesired lightning variation due to temperature variation and/or light source aging, and to account for spatial irregularities inherent to CCD's forming the camera sensors. Calibration procedure first consists of acquiring <<dark>> image signals while obstructing with a cap the objective of the camera 82 for the purpose of providing offset calibration (L=0), and acquiring <<lighting>> image signals with a gray target presenting uniform reflection characteristics being disposed within the inspecting area on the conveyer belt 13 for the purpose of providing spatial calibration. Calibration procedure then follows by acquiring image signals with an absolute reference color target, such as a color chart supplied by Macbeth Inc., to permanently obtain a same measured intensity for substantially identically colored wood chips, while providing appropriate RGB balance for reliable color reproduction. Initial calibration ends with acquiring image signals with a relative reference color target permanently disposed on the calibrating reference support 88, to provide an initial calibration setting which account for current optical condition under which the camera 82 is required to operate. Such initial calibration setting will be used to perform calibration update during operation, as will be later explained in more detail.

As to the moisture sensing unit 78, further calibration steps are carried out, using a chips sample which is subjected to a progressive drying process according to an experimental moisture range that is representative of the actual moisture range, to derive a reference moisture curve through standard measurement in laboratory, such as the curve M shown in FIG. 5. The moisture curve obtained is then compared with a reference chip surface moisture curve obtained with the sensing unit 78, allowing an initial calibration thereof. While the chips sample is being dried, luminance values are also measured to derive a luminance curve associated with the obtained moisture curve, such as curve L shown in FIG. 5. Then, luminance compensation values to be used for the normalization to the predetermined reference moisture value can be obtained through the relation $\Delta l \approx -k\Delta m$, with $\Delta m = m_c - m_r$, wherein $m_c$ is a current chip surface moisture value as measured by the unit 78 and $m_r$ is the predetermined reference moisture value.

Initialization procedure being completed, the apparatus 10 is ready to operate, the computer unit 102 being in permanent communication with the PLC 107 to monitor the operation of the screw drive 28 indicating the presence of a new batch to be inspected. Whenever a new batch is detected, the following sequence of steps are performed: 1) end of PLC monitoring; 2) batch data file reading (species of wood chips, batch identification number); 3) image acquisition and processing for wood chips batch classification according to the set threshold values; and 4) data and image recording after batch inspection. Image acquisition consists in sensing light reflected on the superficial wood chips 26' included in the present batch portion to generate color image pixel data representing values of color components within RGB color space for pixels forming an image of the inspected area defined by camera field of view 80. Although a single batch portion of superficial chips covered by camera field of view 80 may be considered to be representative of optical characteristics of a substantially homogeneous batch, wood chips batches being known to be generally heterogeneous, it is preferable to consider a plurality of batch portions by acquiring a plurality of corresponding image frames of electrical pixel signals. In that case, image acquisition step is repeatedly performed as the superficial wood chips of batch portions are successively transported through the inspection area defined by the camera field of view 80. Calibration updating of the acquired pixel signals is performed considering pixel signals corresponding to the relative reference target as compared with the initial calibration setting, to account for any change affecting current optical condition. Superficial wood chips 26' are also scanned by infrared beam generated by the unit 78, which analyzes reflected radiation to generate the chip surface moisture indication signals. It is to be understood that while the moisture sensing unit 78 is disposed at the output of the inspection station 12 in the illustrated embodiment, other locations downstream or upstream to the inspection station 12 may be suitable.

As to image processing, the image processing and communication unit 118 is used to derive the luminance-related data, preferably by averaging luminance-related image pixel data as basically expressed as a standard function of RGB color components as follows:

$$L = 0.2125R + 0.7154G + 0.0721B \qquad (6)$$

Values of H (hue) and S (saturation) are derived from RGB data according to the same well known standard, hue being a pure color measure, and saturation indicating how much the color deviates from its pure form, whereby an unsaturated color is a shade of gray. As mentioned before, the unit 188 derives global reflection intensity data for the inspected batch, designated before as optical response index with reference to FIG. 6, from the acquired image data. For example, experience has shown that spruce and balsam fir are brighter than jack pine and hardwood, and chip ageing and bark content decrease chip brightness. Calibration updating of the acquired pixel signals is performed considering pixels signals corresponding to the relative reference target as compared with the initial calibration setting, to account for any change affecting current optical condition. Then, image noise due to chip border shaded areas, snow and/or ice and visible belt areas are preferably filtered out of the image signals using known image processing techniques. From the signals generated by moisture sensing unit 78, the image processing and communication unit 118 applies compensation to the acquired pixel signals using the corresponding moisture indicating electrical signals.

Global reflection intensity data may then be derived by averaging reflection intensity values represented by either all or representative ones of the acquired pixel signals for the batch portions considered, to obtain mean reflection intensity data. Alternately, the global reflection intensity data may be derived by computing a ratio between the number of pixel signals representing reflection intensity values above a predetermined threshold value and the total number of pixel signals considered. Any other appropriate derivation method known in the art could be used to obtain the global reflection intensity data from the acquired signals. Optionally, the global reflection intensity data may include standard deviation data, obtained through well known statistical methods, variation of which may be monitored to detect any abnormal heterogeneity associated with an inspected batch.

Whenever a luminance-based classification is desired for the inspected batch of wood chips, the image processing and communication unit 118 compares the global reflection intensity data to reference reflection intensity data including range thresholds, to provide classification of the inspected wood chips batch into a proper wood chip grade according its light reflection characteristics. As mentioned before, reference reflection intensity data may comprise threshold data respectively corresponding to a plurality of wood chip species or a blend thereof. In that case, batch data input device 114 sends to the image processing and communication an electrical signal indicating wood species to which the wood chips of the current inspected batch correspond, and classification is performed by comparing the global reflection intensity data to the reference reflection intensity data corresponding to the selected wood chip species accordingly. Alternately, input device 114 can be in the form of an automated reading device capable of detecting machine readable code associated with the inspected batch, the code representing the corresponding one of wood chip species. In a case where the inspected batch is classified as being acceptable for a given grade, the computer unit 102 resumes PLC monitoring for a next batch to be inspected. Otherwise, whenever an unacceptable batch is detected and therefore rejected, the computer unit causes an alarm to be set by the PLC before resuming PLC monitoring. In operation, the computer unit 102 continuously sends a normal status signal in the form of a <<heart beat>> to the PLC through line 106'. The computer unit 102 also permanently monitors system operation in order to detect any software and/or hardware based error that could arise to command inspection interruption accordingly. Preferably, to save computer memory, the computer unit 102 does not keep all acquired images, so that after a predetermined period of time, images of acceptable inspected batches are deleted while images of rejected batches are recorded for later use. The image processing and communication module 118 performs system status monitoring functions such as automatic interruption conditions, communication with PLC, batch image data file management, dumping monitoring and monitoring status. These functions result in messages generation addressed to the operator through display 132 whenever appropriate action of the operator is required. For automatic interruption conditions, such a message may indicate that video (imaging) memory initialization failed, an illumination problem arose or a problem occurred with the camera 82 or the acquisition card. For PLC communication, the message may indicate a failure to establish communication with PLC 107, a faulty communication interruption, communication of a ((heart beat)) to the PLC 107, starting or interruption of the <<heart beat>>. As to batch data files management, the message may set forth that acquisition initialization failed, memory storing of image or data failed, a file transfer error occurred, monitoring of recorded is being started or ended. As to chips dumping monitoring, the message may alert the operator that batch data has not been properly read, dumping monitoring being started or ended. Finally, general operation status information is given to the operator through messages indicating that the apparatus is ready to operate, acquisition has started, acquisition is in progress, image acquisition is completed and alarm for rejected batch occurred.

Figure 7:
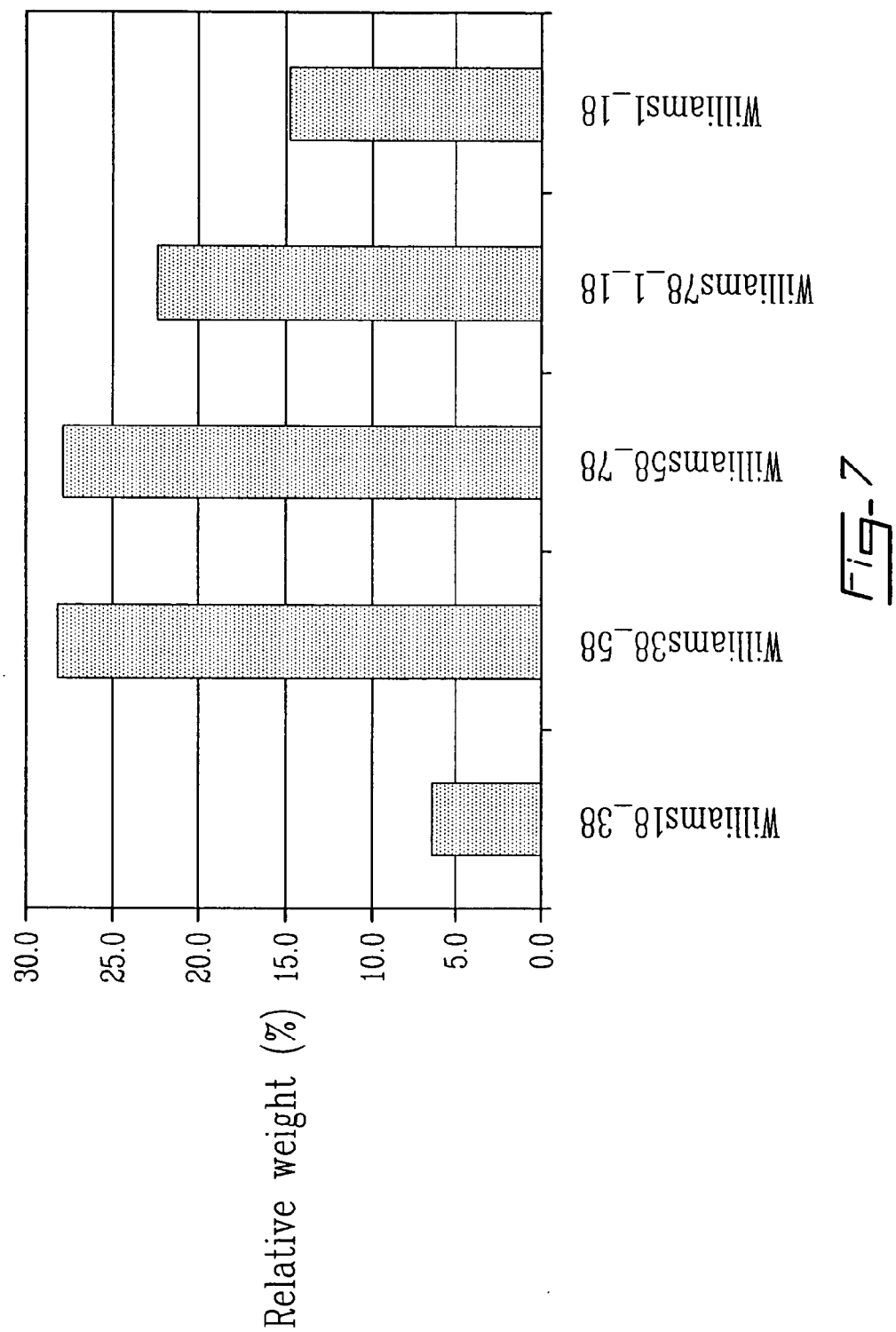
FIG. 7 is a graph showing an example of test results obtained with the Williams grain size classifier.

An online method to obtain chip size distribution Z will now be described with reference to FIGS. 7 to 22. Uniform chip size is very important for the production of high quality pulp. Changes in the distribution of sizes influence chip bulk density under a dynamic feeding condition, and therefore influence the applied specific energy; oversize chips require more energy and produce poor pulp quality; fines and pin chips decrease the pulp strength. Several types of chip classifiers are available for off-line laboratory testing, and few systems may provide on-line discontinue measurements, as discussed by Bergman, T. in "On-line Chip Analysis: New Technology for an Improved Pulping Process", Pulp & Paper Canada, (12) 150-151 (1999). These measurements took only one portion of the wood chip for evaluating the size distribution of all chips, which were not really representative. For example, the well known Williams classifier makes use of superposed sifting trays of decreasing perforations sizes to physically separate the wood chips of a test sample according to increasing grain sizes, to produce a plurality of sub-samples that are subsequently weighted to obtain a weight distribution in function of grain size classes. An example of test results obtained with the Williams classifier is shown in FIG. 7, wherein the grain size class identification is represented as follows:

William18_38: ⅛<size<⅜ in.
William38_58: ⅜<size<⅝ in.
William58_78: ⅝<size<⅞ in.
William78_1_18: ⅞<size<1 ⅛ in.
William1_18: size>1 ⅛ in.

Figure 8:
FIG. 8 shows a wood chips raw image before on-line grain size measurement processing.
Figure 9:
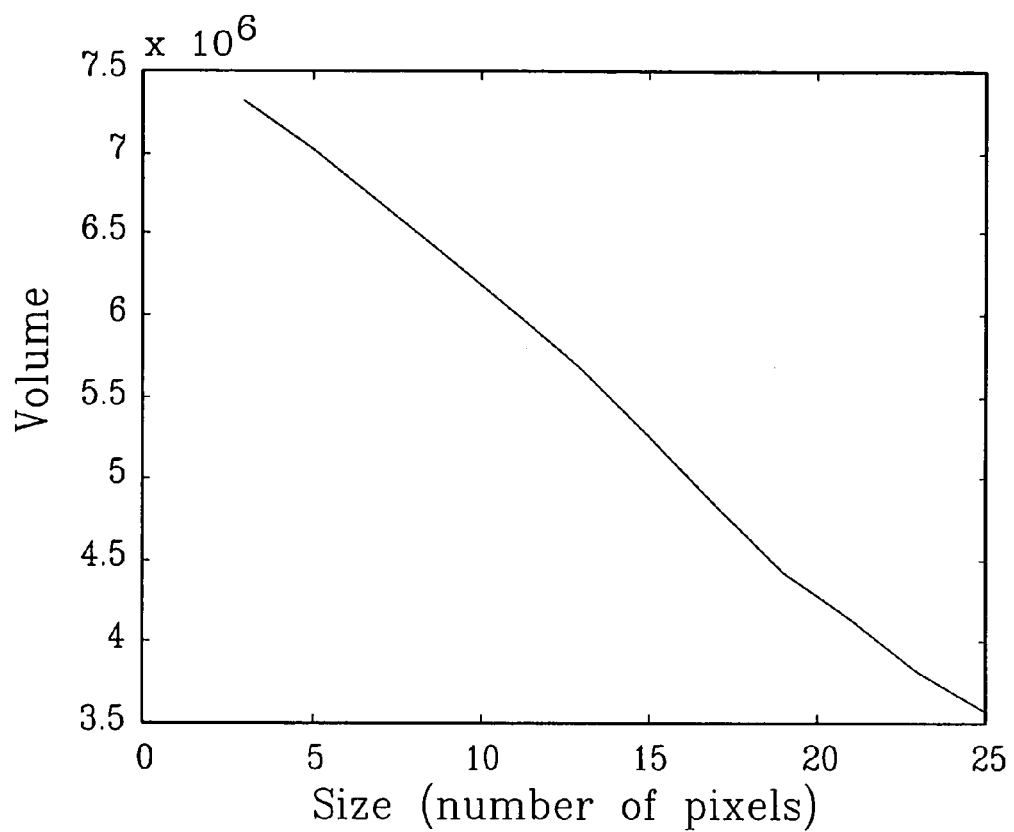
FIG. 9 is a graph representing image volume estimations as a function of all structural elements applied to the image of FIG. 8.
Figure 10:
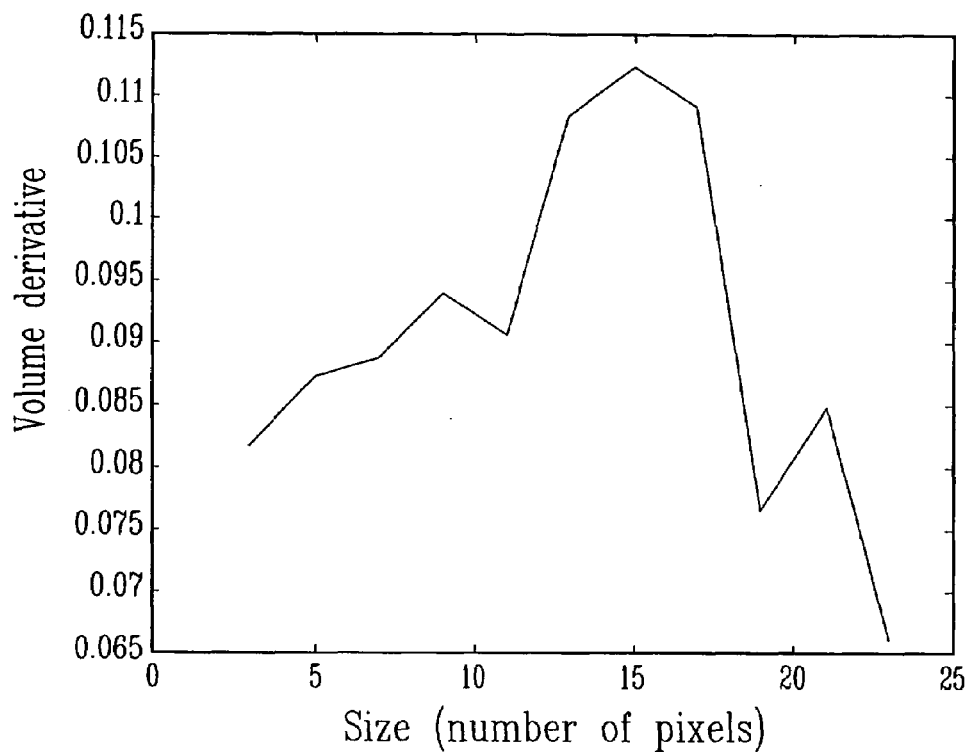
FIG. 10 is a graph representing grain size distribution obtained through derivation calculus from image volume estimation shown in the graph of FIG. 9.
Figure 11A:
Figure 11B:
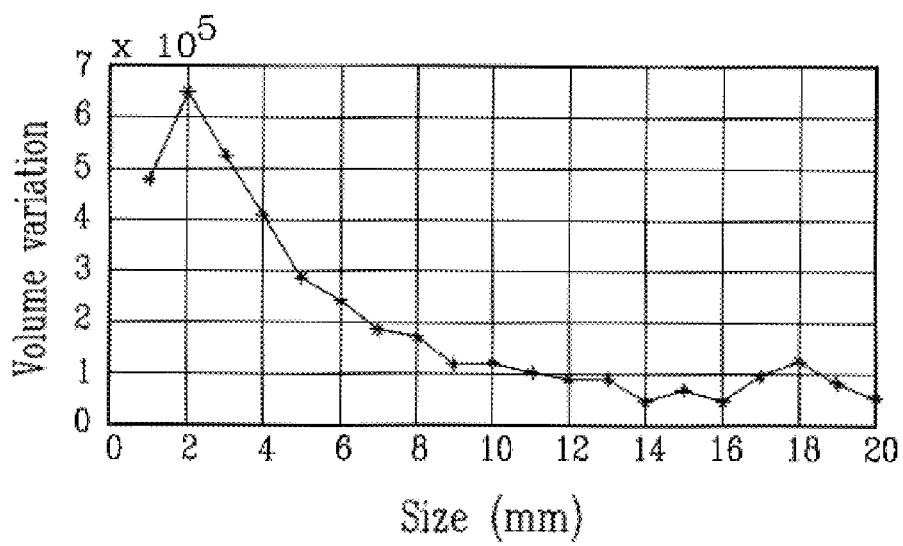
Figure 13A:
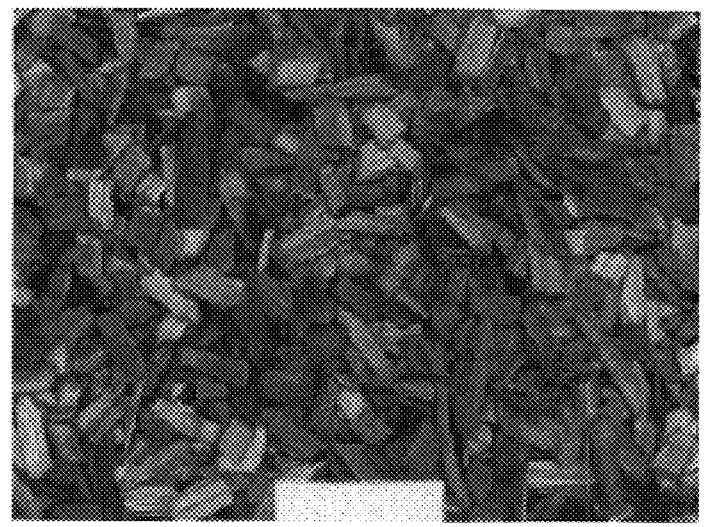
Figure 13B:
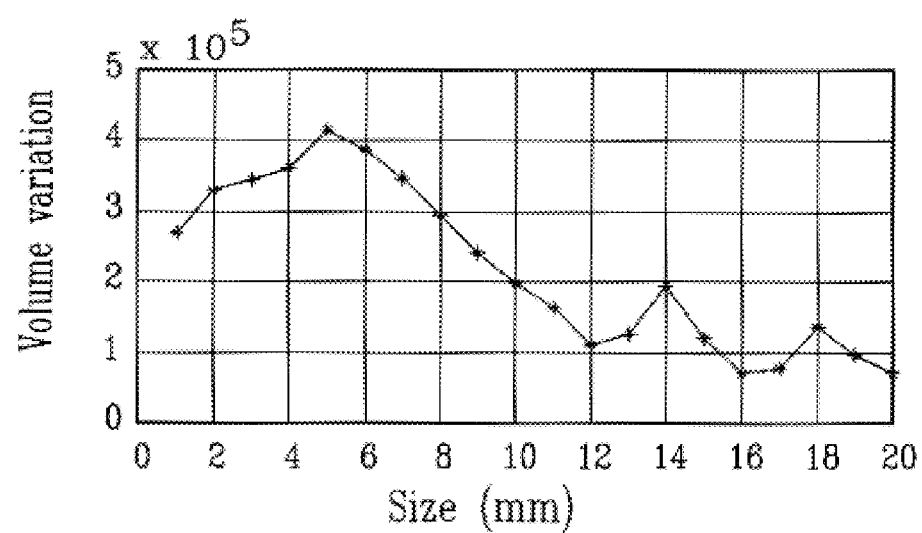
Figure 14A:
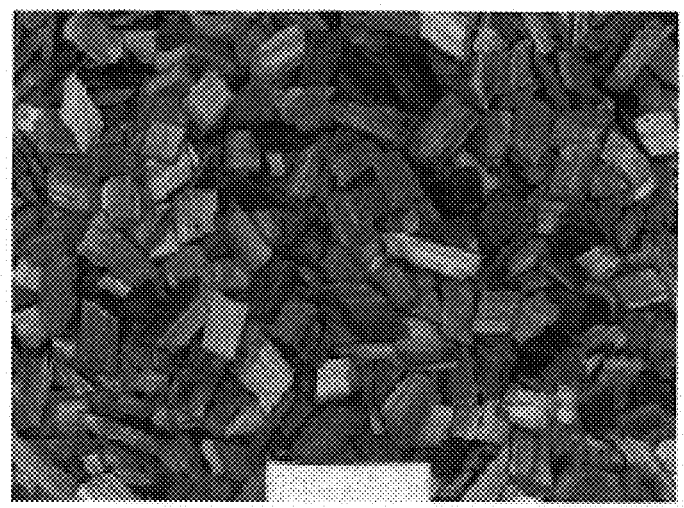
Figure 14B:
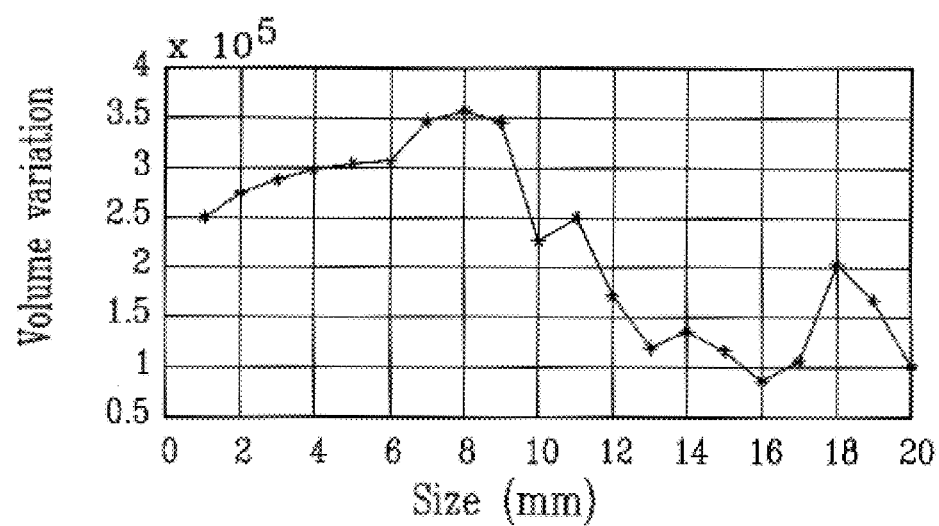
Figure 15A:
Figure 15B:
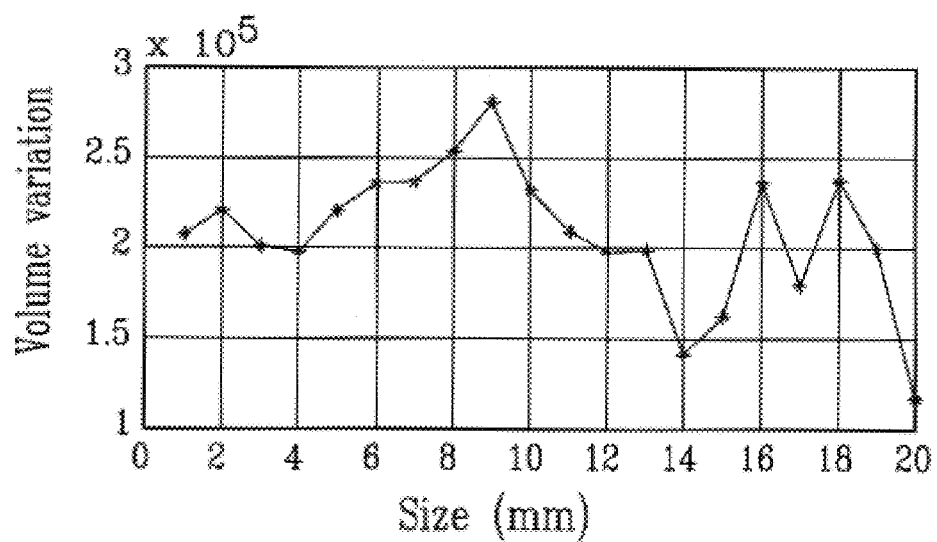
Figure 16:
FIG. 16 shows an image of a typical sample containing wood chips of various grain sizes.
Figure 17:
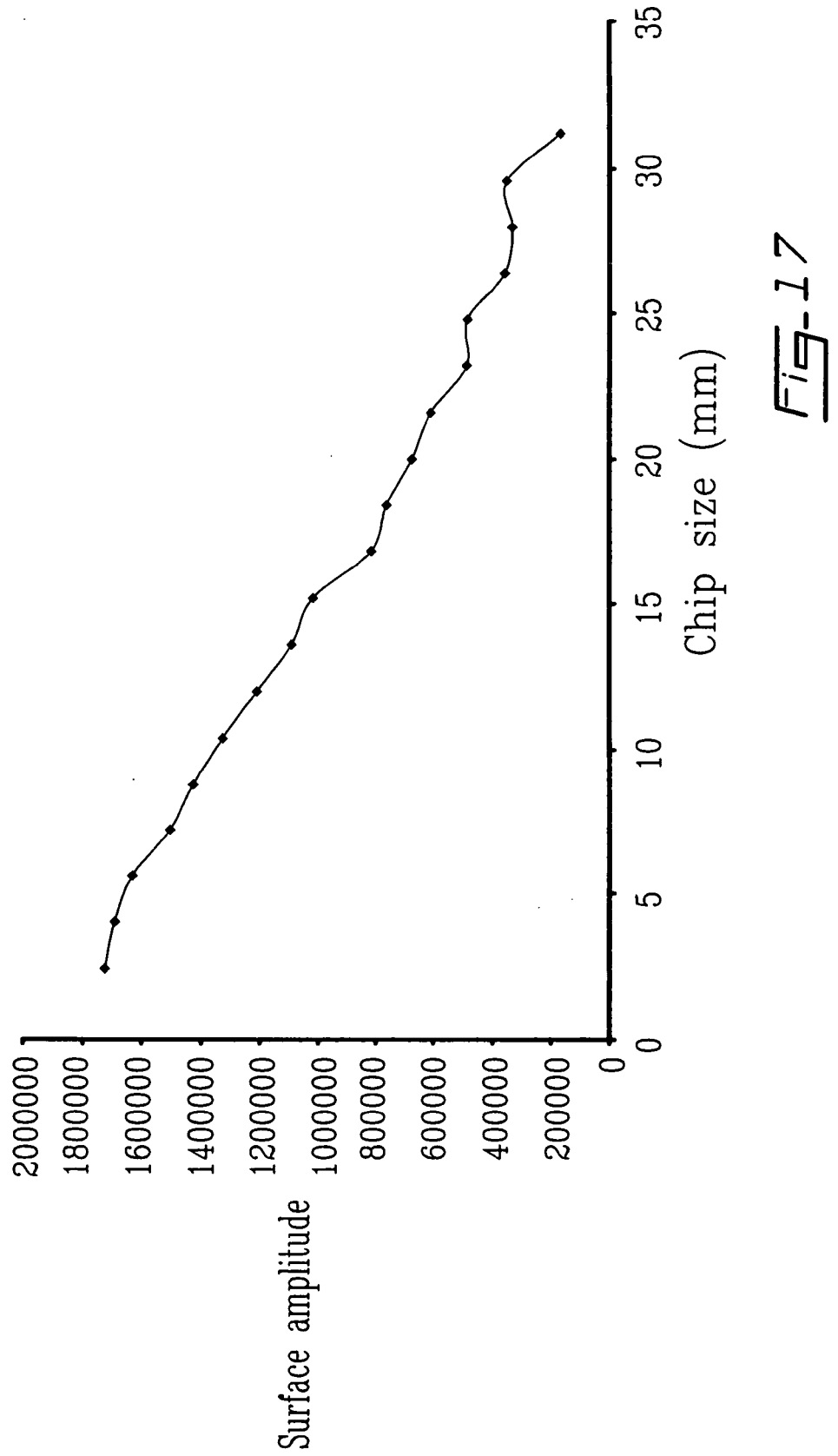
FIG. 17 shows a graph representing grain size distribution for the image of FIG. 16, expressed by surface amplitude as a function of grain size.
Figure 18:
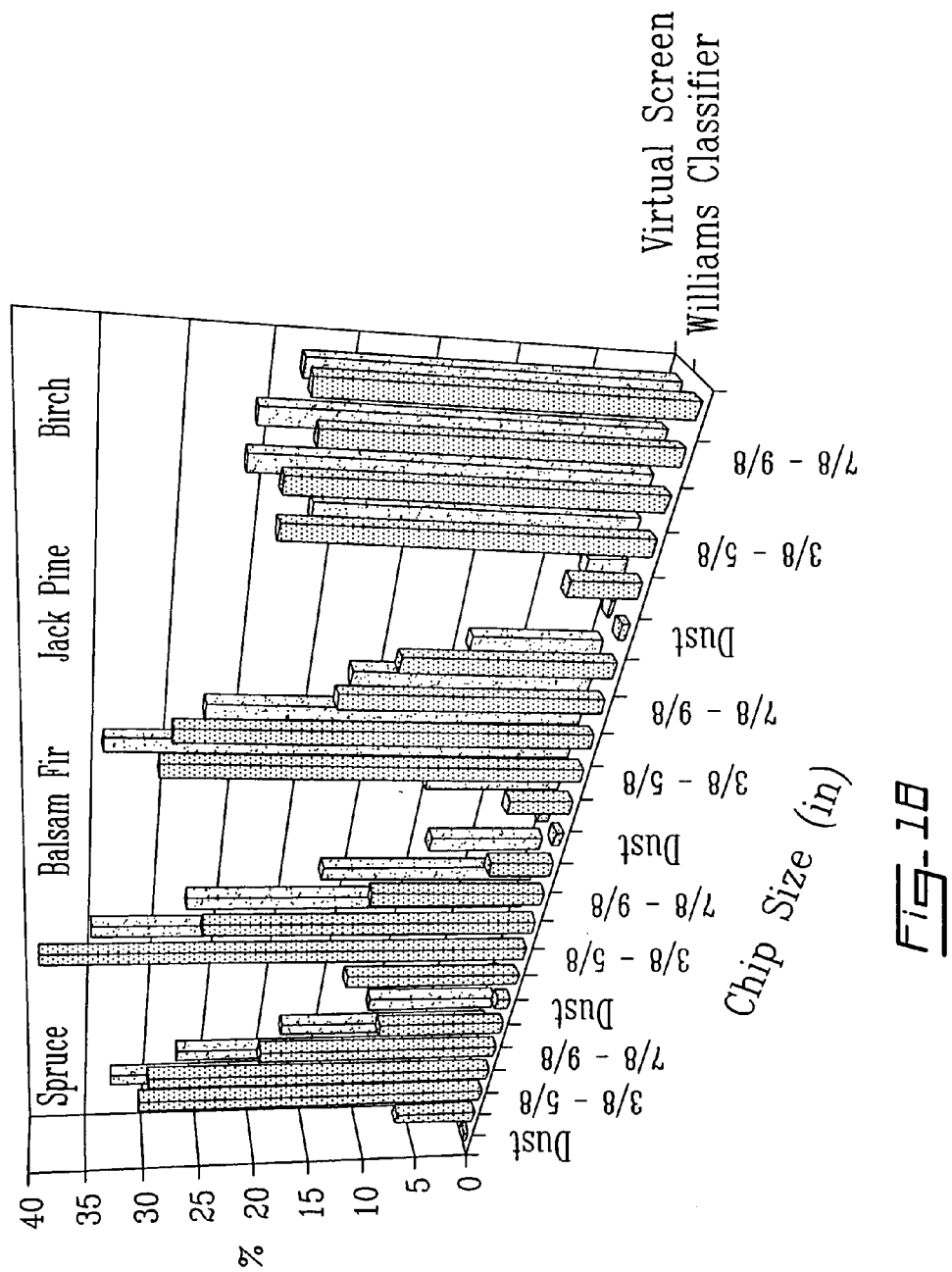
FIG. 18 is a graph in 3D showing the relationship between the proposed image processing-based grain size estimation method and the standard William classifier.
Figure 19:
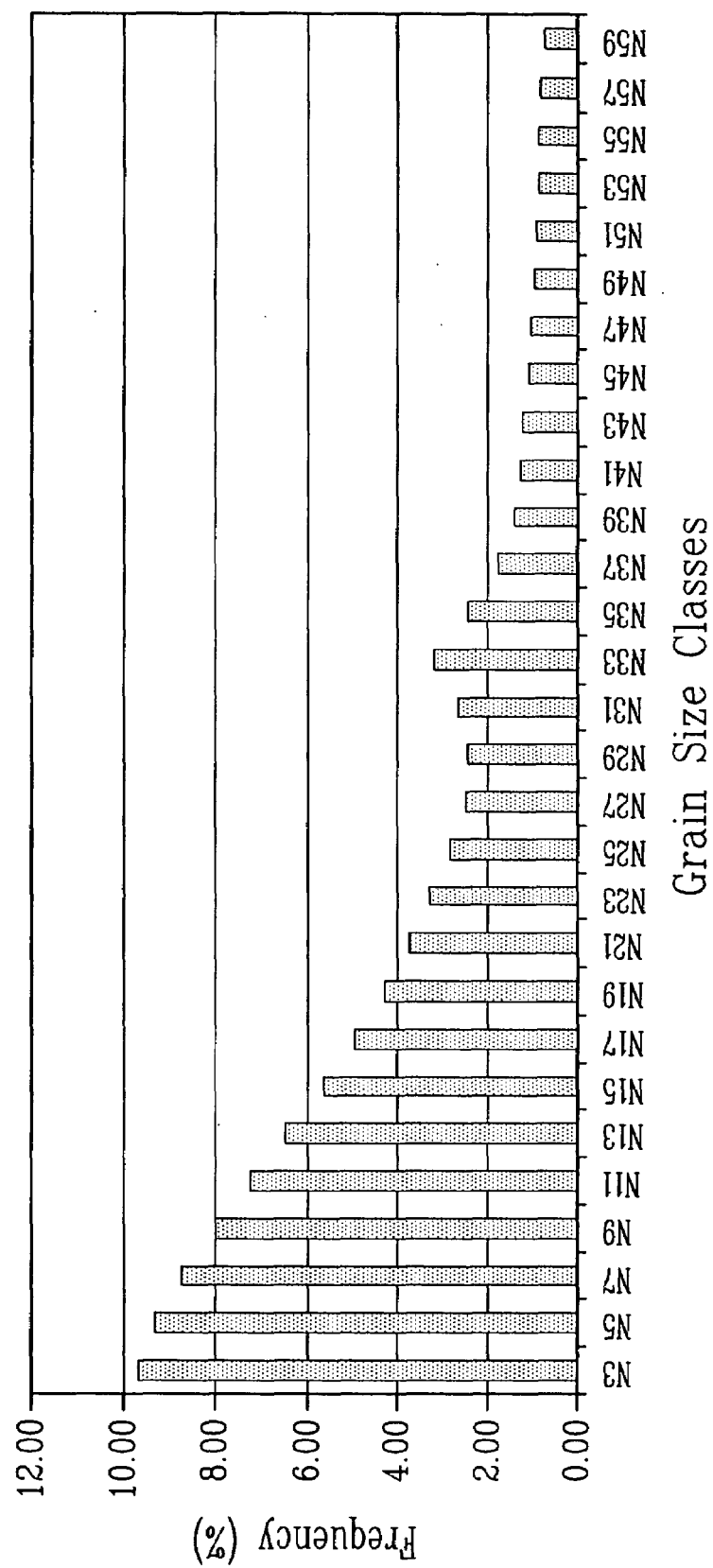
FIG. 19 is another example of grain size distribution corresponding to a typical wood chip sample.

Using a chip classifier such as Williams to classify chip size is frequently performed at chip reception sites of mills, but this offline measurement cannot be conveniently used to stabilize and control a TMP process. In order to perform an on-line chip size distribution measurement, a computerized grain size measurement method using image processing technique is preferably used. The process of computing grain size is similar to sifting sand through a screen. By gradually increasing the screen size, only the larger sand grains will be left at the end of the sifting process. As a result, the number and weight of sand grains can be plotted as a function of screen size. The resulting curve represent grain size distribution of the particles in the tested sample. A similar result may be obtained using an inspection station such as described above wherein the image processing unit is programmed to generate a size distribution of the particles visible in the acquired images, using known mathematical morphology techniques, whereby an image is opened using a set size of.structuring elements, as described by Matheron, G., IN "Random Sets and Integral Geometry", John Wiley & Sons, New York (1975), Vincent L., in "Granulometries and Opening Trees", *Fundamenta Informaticae*, 41, 57-90 (2000), Maragos, P., in "Pattern Spectrum and Multiscale Shape Representation", IEEE Trans. PAMI, 11(7), 701-716 (1989), and Soille, P., in "Morphological Image Analysis: Principles and Applications", Chap. 4, Springer-Verlag (1999). Each successive opening is performed using a larger structuring element. As long as the smallest dimension of a wood chip is not contained by the structuring element, that wood chip will not be assigned the class corresponding to the current grain size and will pass to the next step. Such morphological approach is particularly efficient since the wood chips are superimposed according to various spatial orientations in 3D. It is therefore reasonably assumed that wood chips in the processed image are substantially of homogeneous dimensions in all main axis generally defining width and length are substantially rectangular so that the smallest dimension projected on either main axis is considered for the purpose of image filtering. After a preset number of iterations, the size distribution or histogram of the wood chips visible in the image as a particular texture is obtained. A resulting graph can be obtained showing the proportion of pixels that contributed to that filtering size, as will be explained later in more detail. The proportion of pixels is directly correlated to the number of wood chips of that size. According to the proposed image processing technique, light is directed onto an inspected area of the wood chips, using electrical light units 96 of inspection station 12 of FIG. 3. Then, light reflected from the inspected area is sensed by camera 82 to generate image pixel data forming an image of the inspected area. Such wood chips raw image is shown in FIG. 8. For the purpose of size measurement, image pixel coordinates are transformed in corresponding physical, dimensional units, on the basis of proper calibration of the camera 82, as well known in the art. Furthermore, geometrical aberrations due to inherent defects of optical components provided on the camera 82 are corrected through calibration steps using a standard calibration grid, as also well known in the art . Having previously defined a first structuring image element of a first, smallest predetermined size (typically a number of pixels in a square configuration) this first element is applied (convoluted) to the image to identify groups of pixels defining a structure characterized by a minimal dimension substantially contained within the image element, wherein these groups of pixels are associated with substantially individual wood chips. Then, the cumulative number of pixels contained within these identified group of pixels is estimated to provide an image surface or volume estimation, and they are then filtered out from the image to generated a filtered image. Having defined a further structuring element of predetermined size larger than the first predetermined size, and other further structuring element of increasing size, until a predetermined maximum structuring element size is defined, the preceding processing steps are repeated in a iterative manner using such further structuring elements of increasing size along with successively obtained filtered images, until the maximum structuring element size is used. Finally, the wood chips size distribution or image size spectrum is obtained from successively estimated cumulative numbers of pixels. For so doing, image surface or volume estimations as a function of all structural elements applied to the image, as shown by the exemplary graph of FIG. 9, give through derivation calculus the desired grain size distribution as shown by the corresponding graph of FIG. 10. FIGS. 11a, 12a, 13a, 14a, 15a show images of wood chips sub-samples that were obtained through successive sifting steps to group wood chips according to complementary ranges of sizes, while FIGS. 11b, 12b, 13b, 14b, 15b are corresponding graphs showing the behavior of volume variation as the size of wood chips increases. FIG. 16 shows an image of a typical sample containing wood chips of various grain sizes, and FIG. 17 shows graphically the corresponding grain size distribution, expressed by surface amplitude as a function of grain size (chip width). It can be seen from FIG. 17 that there are more smaller chips than larger chips in the tested sample. The wood chips being in random orientation, it can be shown that the relative volume estimation error may have a value between 0% and 29,29% (for ±45°, ±135°). Wood chip fibers orientation following chip width and length in a random manner, chip width is a good indicator to fibers' length. Furthermore, chip width measurement allows to estimate small size chip content, which contribute to adversely affect pulp quality. The proposed method can be readily implemented by anyone skilled in the art of computer programming using known application development software such as MatLab™ from Matworks (Natick, Mass., USA), or known high level programming software such as C++ with ActiveMill image processing library. While the proposed uni-dimensional grain size estimation algorithm is advantageously simple to implement, it is to be understood that other more complex image processing techniques, such as 2D or 3D approaches, or a combination of the proposed method and any such technique, can be used to perform grain size measurement as required by the quality estimation model of the present invention. For example, a segmentation algorithm may be used to locate and identify in 2D or 3D the borders of individual wood chips in the image for the purpose of estimating grain size distribution. The proposed method calculates the percentage of number of pixels for certain size chips on total pixels of the images, which is different to Williams classifier that calculates the percentage of weight for certain size chips on total weight of the chips. Therefore, these two methods cannot be compared directly. Using known PLS (Projection on a Latent Structure) modeling, the relationship between the two methods can be analyzed, and exemplary validation test results for four different wood species, namely spruce, balsam fir, jack pine and birch, are plotted in FIG. 18. Such relationship may also be defined analytically as will be now explained in detail with reference to FIGS. 19 to 22. Referring to the graph of FIG. 19, the grain size distribution corresponding to a typical wood chip sample is shown, wherein $N_3$ (3 pixels×3 pixels ), $N_5$ (5 pixels×5 pixels) . . . $N_r$ (r pixels . . . r pixels) . . . $N_{59}$ (59 pixels×59 pixels) represent the size of the square structuring element used to perform successive image convolutions for each corresponding grain size class. The relative weight $P_r$ of a class $N_r$ may be approximately expressed as follows:

$$P_r \approx nV \quad (7)$$

wherein n is the number of wood chip in the group to which the class Nr is assigned, V being the average volume of a wood chip. Assuming in a first approximation that the volume of a wood chip may be comparable to a corresponding sphere, we have:

$$V \approx r^3 \quad (8)$$

The number of wood chip may be roughly estimated as follows:

$$n \approx \frac{N_r}{r^2} \quad (9)$$

Grouping the above relations (7) and (8) into relation (6), the relative weight of a grain size class r may be obtained with the following ramp transformation:

$$P_r = rN_r \quad (10)$$

with:

$$\sum_r P_r = 100 \quad (11)$$

Figure 20A:
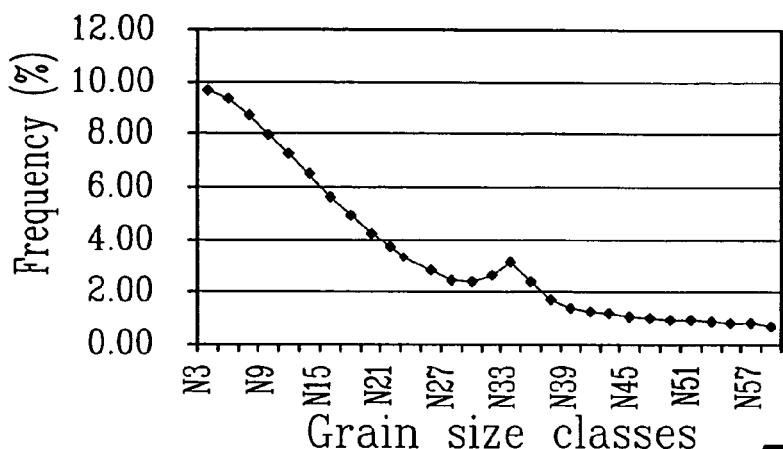
FIGS. 20a-20c are graphs showing a proposed ramp transformation to obtain a resulting chip relative weight distribution from a volume-based distribution.
Figure 20B:
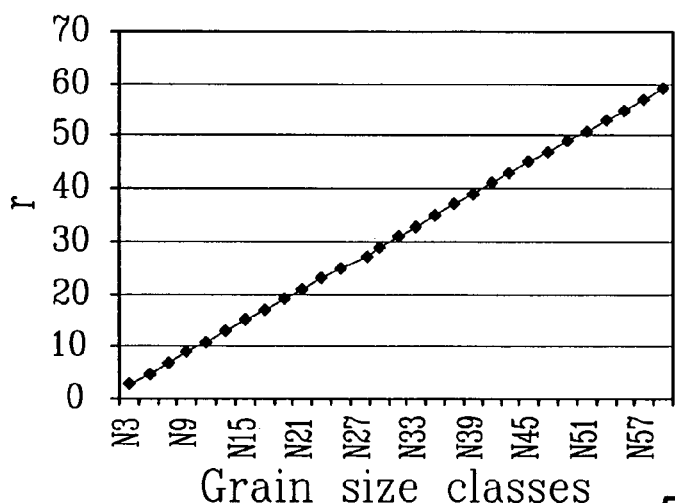
Figure 20C:
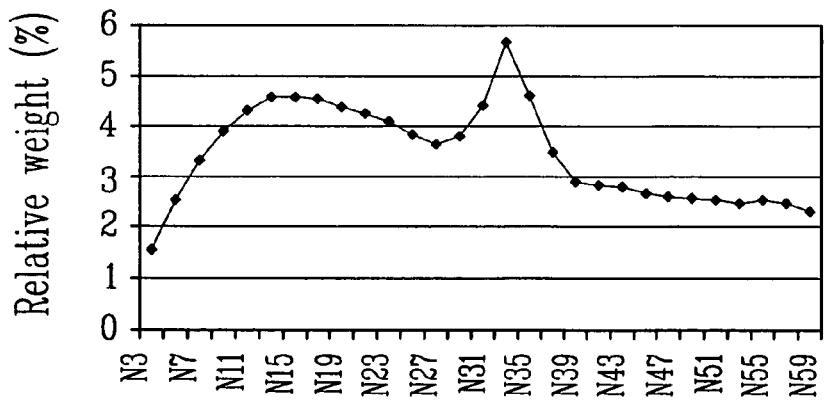
Figure 21:
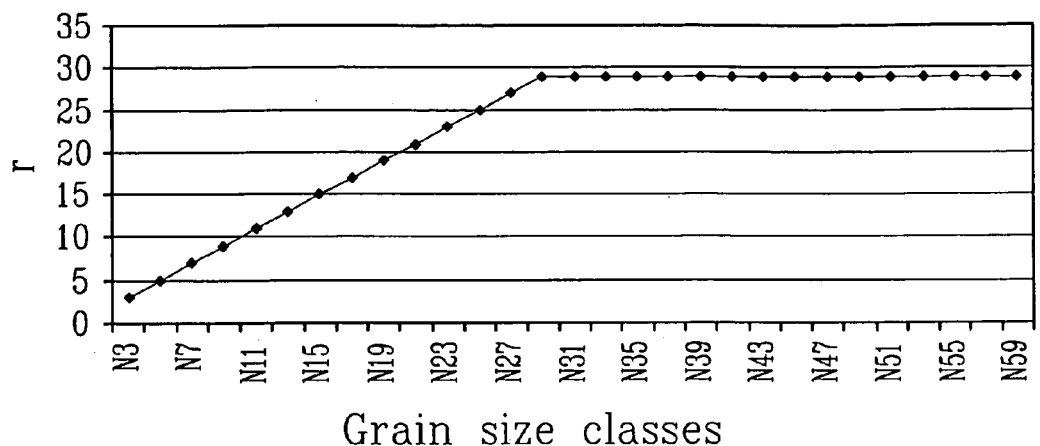
FIG. 21 is a graph representing an alternate ramp-based function to perform the transformation.
Figure 22:
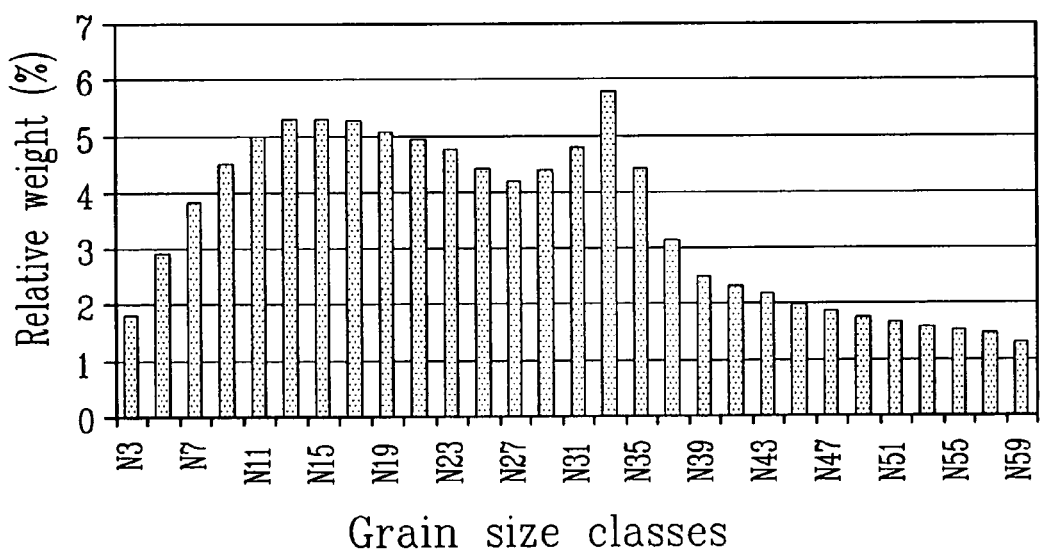
FIG. 22 a graph representing a resulting relative weight distribution using the alternate ramp of FIG. 21.

Such transformation is illustrated by the graphs of FIGS. 20a and 20b that are combined to obtain a resulting relative weight distribution shown in FIG. 20c. Since the wood chips are not actually spherical, a maximum value for the ramp may be chosen to reflect limited chip thickness, as shown in the graph of FIG. 21, to obtain a resulting distribution as shown in the graph of FIG. 22, which clearly presents similarities with a typical weight distribution that can be obtained with the William classifier.

Figure 23:
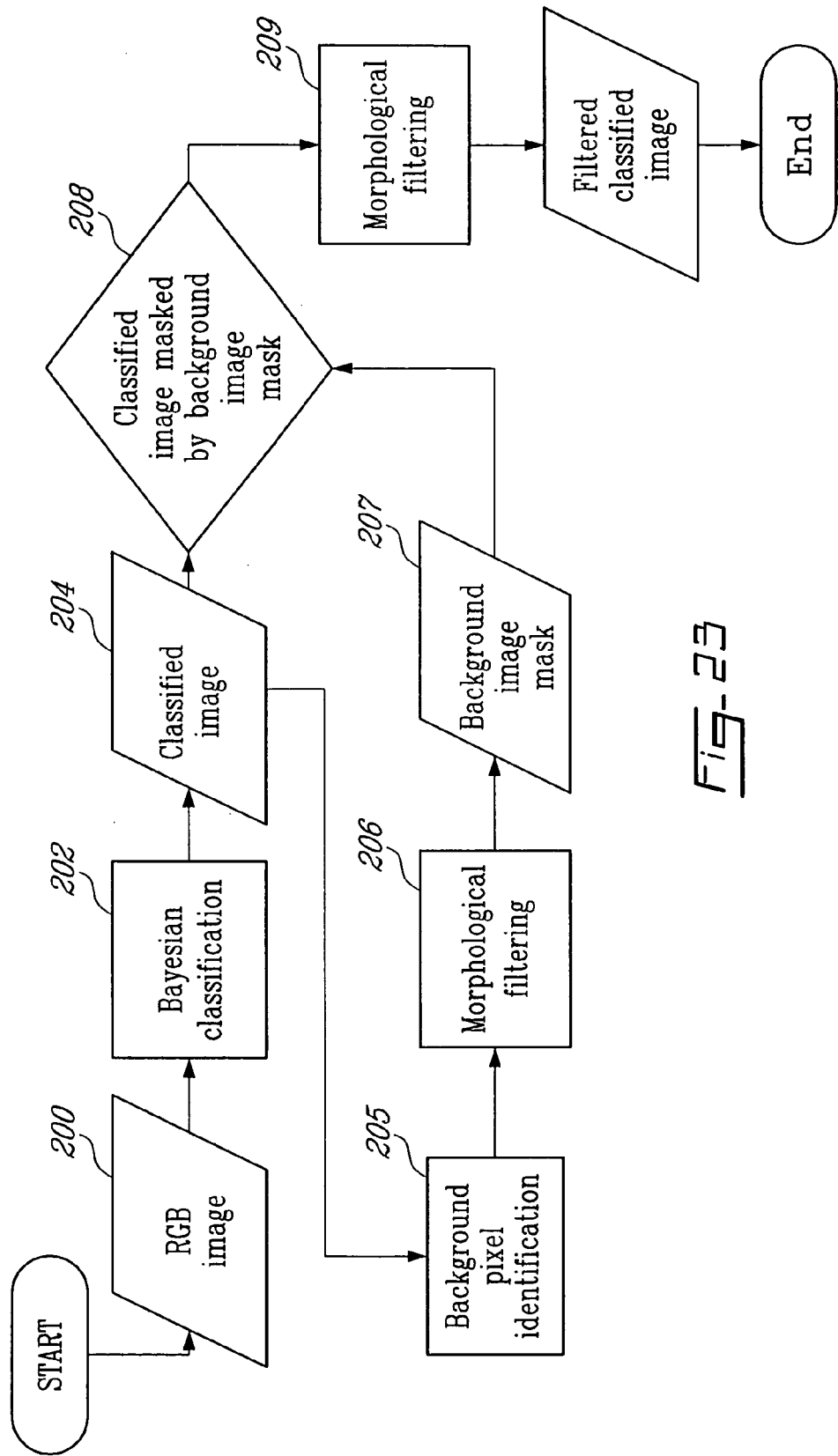
FIG. 23 is a block diagram of chip impurities learning-based detection method that can be used according to the chip quality estimation method of the invention.
Figure 24A:
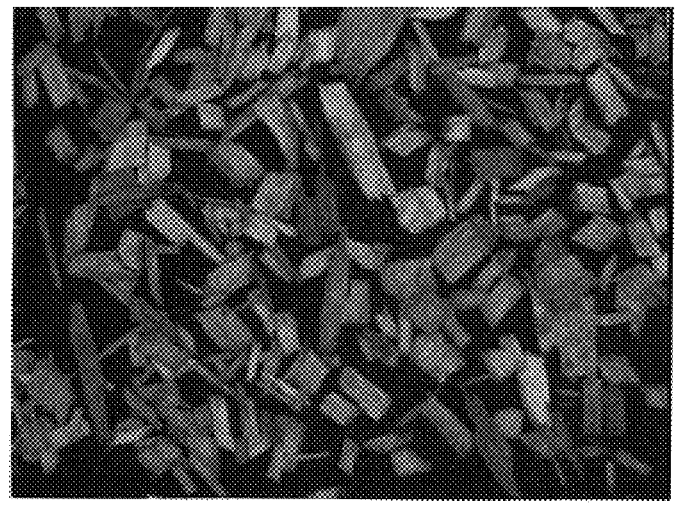
FIG. 24a-24d are a raw images of spruce chips before processing using the proposed impurities detection method.
Figure 24B:
Figure 24C:
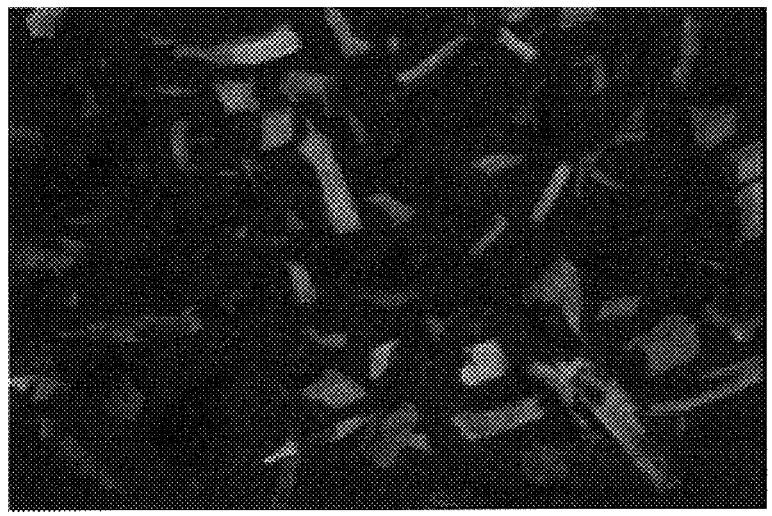
Figure 24D:

According to another aspect of the model defined by the general relation (1) above, the considered properties may further include impurities content characterizing the wood chips, including bark, rot and knot, or other contaminants such as plastic, rubber or metal fragments initially contained in the wood chips. Bark content is a particularly critical factor in the production of a high quality pulp. Excessive bark content will give rise to problems of pulp brightness, strength. and paper quality. As bark color is generally darker than chip color, it is possible to discriminate them in bark-chip mixtures. Basically, using the inspection station described before, the impurities content can be estimated using a color classification technique including the steps of: a) directing polychromatic light onto an inspected area of the wood chips; b) sensing light reflected from the inspected area to generate color image pixel data representing values of color components within a color space for pixels forming an image of the inspected area; c) comparing the image pixel data with color classification data related to the impurities to identify the pixels likely to be associated with the presence of impurities in the inspected area; and d) comparing respective numbers of impurities associated pixels and the image forming pixels to provide the estimated impurities content. A variety of detection methods can be applied. For example, one can pick a color plane such as H, S, L, R, G, B, or any linear combination of them, and select a bark specific intensity range. An image region will be classified as bark if the majority of its pixels fall inside the limits of this bark range. Another method would be to define one or more bark color reference points with an admissible tolerance in the 3D RGB color plane. When the distance from the pixel being classified and the related reference is less than the allowable tolerance, it is classified as bark. However, these two methods need a lot of manual tuning to attain a reasonable confidence level. Such tedious classifier setup can be avoided using a learning method. such as a Bayesian color classifier has been used. It is based on well known probability analysis methods in which the Gaussian statistical distribution for each class can be established. Such learning method presents numerous advantages. It does not require much manual tuning, being statistically based it allows estimation of measurement accuracy, and it provides real time classification. In order to train the algorithm, chip, bark (or other impurities), and belt zone samples are selected from a series of chip images. During training, the algorithm uses them to define corresponding color classes. Such algorithm has proved to be capable of identifying these three color classes from a chip image. Image noises (snow specks) apparent in the classified image can be filtered out using morphological post-processing. A more detailed description of the proposed learning-based impurities classification method will now be described with respect to FIGS. 23-35b. Such method can be carried out using the optical inspection station as described above. Referring to FIG. 23, the proposed method starts with the acquisition of RGB image designated at 200. Such raw images are shown in FIG. 24a for sound spruce chips, in FIG. 24b for spruce chips containing knots, in FIG. 24c for spruce chips containing bark and in FIG. 24 for spurce chips containing rot. It is to be understood that other color space such as LHS or LAB may also be used. Then, a Baysian classification is applied at step 202 to the acquired image to generate a classified image at 204. The Baysian color classifier is used to identify dark portion of the image associated with impurities, in contrast with clear portion generally associated with sound chips. The classifier has also the task of identifying image background that must not be associated with impurities. The classifier may be readily implemented by anyone skilled in the art of computer programming in the form of a software allowing the user to define the image to be used at the training stage, as well as the color classes to be detected. The user can select image areas to form a set of training prototypes. The software is programmed to analyze statistical distribution of RGB pixel values and configure the classifier accordingly, to generate a truth look-up table assigning one of the predetermined color classes to each possible RGB value. As explained in more detail by Fukunaga in "Introduction to statistical pattern recognition" Academic Press, 1990, a Bayesian classifier may be implemented by obtaining statistical distribution data representing values of color components within the chosen color space that characterize each impurity, employing a training strategy wherein a set of samples for each class of impurity is subjected to light inspection, so that the distribution of the color components values given by the color image pixel data may be calculated. Preferably, samples of non-contaminated wood chips and contextual elements such as conveyor belt material, are also considered at the training step, to adjust classification parameters more accurately. Assuming that the resulting distributions characterizing all impurity classes are substantially Gaussian, the classifier obtained as a result of the preliminary training process may then be used to estimate a probability that new pixel data be associated with any given color class that has been considered in the training step, each said class indicating the presence of a specific impurity. In the general case involving a plurality of distinct classes of impurities, classification color data is derived from the statistical distribution data through Bayesian estimation of a plurality of probability values that each pixel be associated with the presence of the impurities, for then selecting the statistical distribution having the highest probably value, to identify a pixel as to be likely associated with the presence of the impurity characterized by the selected statistical distribution. The probability that a given pixel of value x={r,g,b} or x={l, a, b} be associated with a color class $\omega_i$ within i=1,N (assuming that all classes are evenly probable) can be expressed as follows:

$$p(x \mid \omega_i) = \frac{1}{\sqrt{2\pi|k_i\Sigma_i|}} \exp\left(-\frac{1}{2}(x-\mu_i)_T(l_a\Sigma_i)^{-1}(x-\mu_i)\right) \quad (12)$$

wherein:
  $\mu$i is mean color component vector for color class $\omega_i$;
  $\Sigma$i is covariance matrix for color class $\omega_1$; and
  $k_i$ is a scale parameter for color class $\omega_i$.

Figure 25:
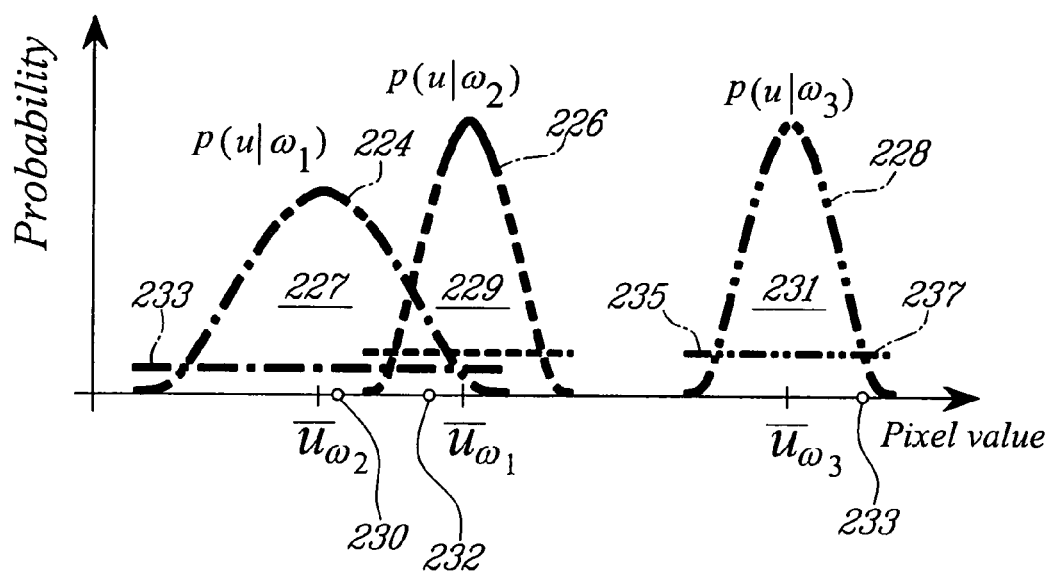
FIG. 25 is a graph representing probability as a function of a color component, illustrating the classification principle of a Baysian classifier.

It can be appreciated that the space area delimited by the envelope or shell defining each impurity class may be either reduces of expanded by adjusting the value of scale parameter $k_i$ as part of the training process, so as to either restrict or widen the selection of pixels for the color class considered. Typically, the value for scale parameter $k_i$ can be selected within the ranges of $0<k_i<1$ to restrict or $k_i>1$ to widen, depending on the outcome of the training process. Once the distribution for each impurity color class has been established in the chosen color space, a probability threshold for each class is preferably defined and applied to validate if the estimated probability in the case of a single impurity classification (such as bark only), or the highest probability value for the selected distribution in the case of multiple impurities classification, is nevertheless sufficient to represent a reliable classification result. Hence. a given pixel defined by specific coordinates in the color space will be assigned to a candidate class only if the estimated or highest probability value for a given pixel is found to be greater than the predetermined probability threshold. Typically, the value for such probability threshold can be selected from 0% to 100% of the distribution's maximum peak, depending on the outcome of the training process. Referring to FIG. 25, an example involving three known impurities to which are associated three color classes designated by $\bullet_1$, $\omega_2$, $\omega_3$, whose envelopes characterizing by maximum probability p<u|$\omega_1$>, p<u|$\omega_2$>, p<u|$\omega_3$> at mean color component pixel values $\overline{U_{\omega_1}}$, $\overline{U_{\omega_2}}$, $\overline{U_{\omega_3}}$ and generally designated at 224, 226, 228 delimit respective classification areas 227, 229, 231 within the selected color space, will be. now discussed. Although a set of single color component curves is represented in FIG. 25 for the sake of clarity, three color components are preferably involved, which are defined within a corresponding three-dimensional color system. While the color components may be defined in standard RGB color space, LAB color components are preferably derived by the data processor unit of the inspection station from RGB color data received from the camera, since they approximate the human eye color sensitivity and give somewhat better classification. It can be seen that to each class area 227, 229 and 231 is associated a corresponding minimum probability threshold represented by lines 233, 235 and 237 in FIG. 3. In the example shown, pixels 230 and 232 as expressed in basic LAB color components are respectively assigned to classes 224 and 226, while pixel 233 is excluded from the classification. According to the preferred validation step as explained above, pixel 233 was rejected since class 228 to which pixel 233 has the highest probability to belong, does not comply with the minimum probability threshold condition. The look-up table containing the color classification data is built by first registering at table input pixel coordinates data (RGB components values corresponding to the LAB components values calculated at the training operation) as well as associated class identification data as output data. Then, all remaining pixel coordinates data, up to the total number of about 16×10⁶ pixel coordinates, are registered at table input and associated with a general sound chip class at table output The training and parameter setting software, as well as the look-up table based classification software may be readily programmed by any one skilled in the art of computer programming. Although a look-up table is preferably built in order to minimize the processing time required for the classification of the pixels in a complete image, which typically includes 76,800 pixels for a 320×240 image, it is to be understood that any other appropriate numerical or analytical technique for generating a classification result for any given pixel on the basis of the statistical distributions obtained through the training process, is contemplated to obtain color classification data according to the method of the invention. Referring now to FIGS. 26a-26c, the computer generated screens shown present the basic statistical parameters (mean values, covariance values, scale factor) for a basic class structure consists of three basic classes, namely "background" in FIG. 26a, "dark" areas associated with impurities in FIG. 26b and "sound" wood chips in FIG. 26c.

Figure 27:
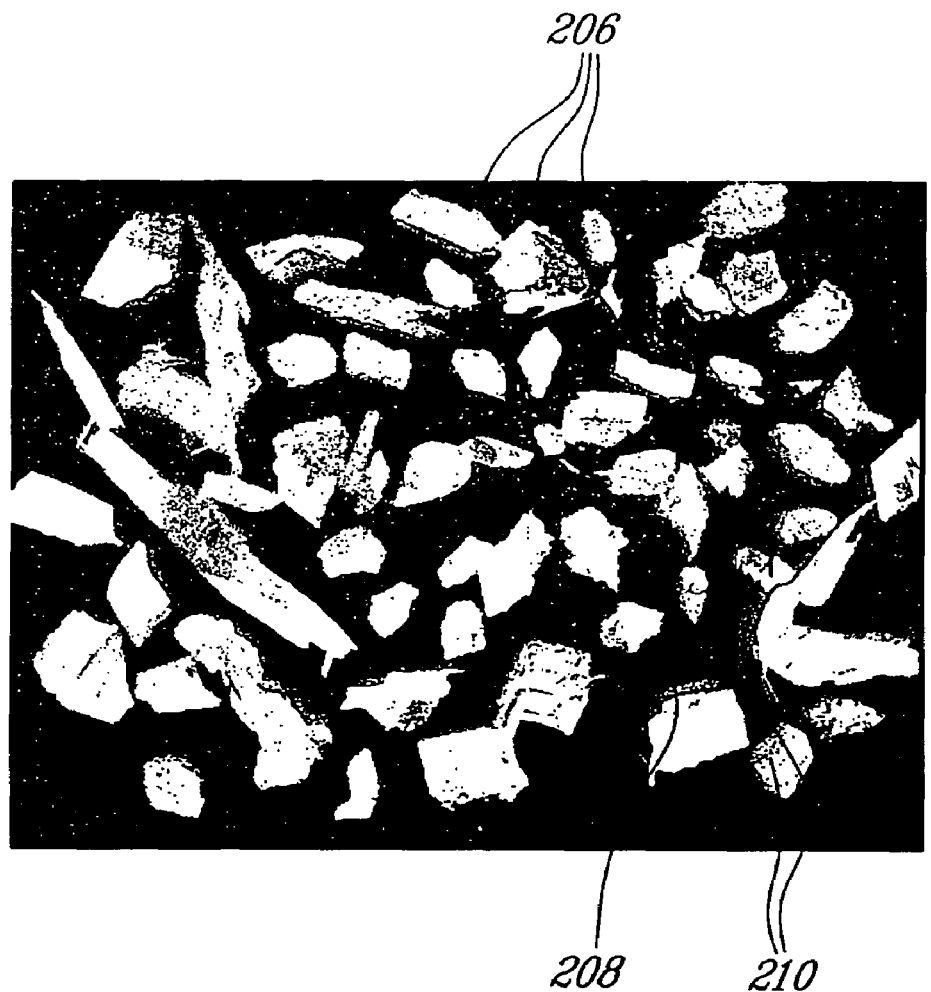
FIG. 27 is an exemplary wood chips image containing a quantity of white noise pixels.
Figure 28:
FIG. 28 is resulting background image mask corresponding to the image of FIG. 27.
Figure 29A:
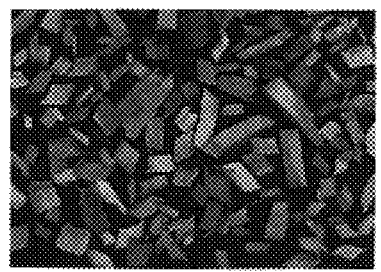
Figure 29B:
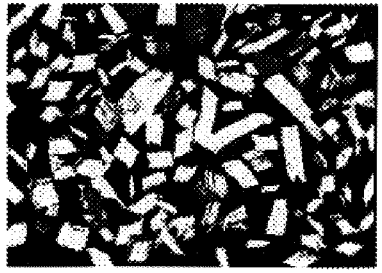
Figure 30A:
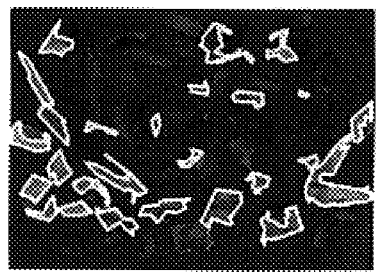
Figure 30B:
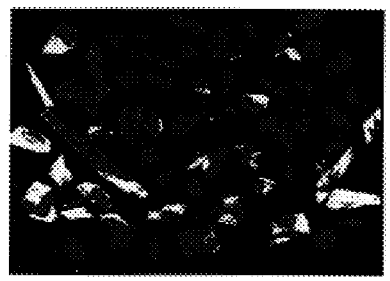
Figure 31A:
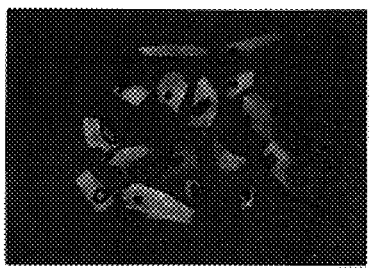
Figure 31B:
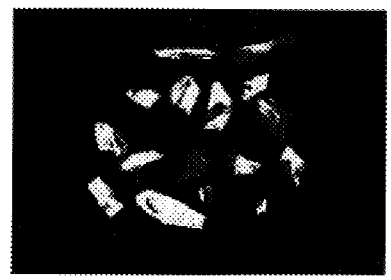
Figure 32A:
Figure 32B:
Figure 33A:
Figure 33B:
Figure 34A:
Figure 34B:
Figure 35A:
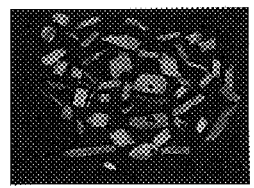
Figure 35B:
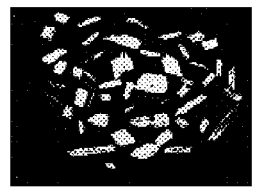

Referring back to FIG. 23, a technique to obtain a background image mask to be applied to the classifier image 204 can be obtained will now be explained. Background pixel segmentation is performed on the basis of pixels that were previously classified as "background" with the Baysian classifier, as indicated at step 205 in FIG. 23, which pixels are nevertheless not used directly since they contain a quantity of white noise pixels 206,208 shown in the image of FIG. 27, which can be respectively associated with wood fines and shade areas. Moreover, other noise pixels to be not confounded with "background" are present on wood chip areas as indicated at numeral 210 on FIG. 27, corresponding to very dark wood chip areas. A proposed morphological filtering sequence designated at step 206 in FIG. 23 to filter these noise pixels is as follows: (1) isolated, contrasting pixels are removed; (2) groups of white pixels (regardless holes that they may contain) characterized by a surface smaller that a predetermined value (ex. 400 pixels²) for a sound chip are deleted, to remove traces left by sound chip fines; (3) shades areas are removed through a morphological process using a majority criterion; (4) "background" pixels on sound chips are removed by analyzing the surface of any hole contained within each group of white pixel, using a minimum threshold (ex. 10 pixels² pi) under which a hole is filled with white pixels; and (5) masking chip border areas that contain darker, sound pixels to avoid false impurity detection, by performing dilatation with a 3×3 core, to obtain the background image mask designated at 207 in FIG. 23. In FIG. 28, an example of resulting background image mask corresponding to the image of FIG. 27 is shown. Then, at step 208, the background image mask is applied to the classified image according to a set of rules such as presented in Table 3:

TABLE 3

| Bayesian classification | Background mask | Result |
|---|---|---|
| Background | Background | Background |
| Background | Other than background | Reject |
| Other than background | Background | Background |
| Other than background | Other than background | Other than background |

The resulting image from which the background pixels have been removed is subjected to a further morphological filtering step at 209 indicated at FIG. 23, to identified and filter out groups of pixels covering small areas (ex. 10 pixels and less). Finally, the classification of remaining pixels is compared with validation selections obtain through the same learning process as explained above. A resulting classification confusion matrix is obtained, such as the one shown in Table 4:

TABLE 4

|  | SOUND | DARK | Reject | Total |
|---|---|---|---|---|
| Sound | 88.1% | 9.6% | 2.3% | 2497950 |
| Dark | 14.8% | 80.0% | 5.2% | 645923 |

Wherein each row corresponds to the actual class designated in the first column, each following column corresponding to the classification obtained., without considering the image background. FIGS. 29a to 35a show a series of exemplary raw images to be classified, wherein some selection made therein, for species of birch and spruce, involving sound chips as well as chips containing impurities (bark, knot, rot). FIGS. 29b to 35b show corresponding classified images wherein the detected impurities are represented in contrast, indicating a good classification performance. It is to be understood that other impurities such as plastic bag or plastic, rubber, and/or metal fragment in chips can also be detected by a properly trained algorithm such as described above, provided an adequate color difference between impurities and chips is present Cases where the properties considered by the quality estimation model further include moisture content characterizing the wood chips will now be described in detail. In the TMP, chips are washed in hot running water and steamed at a high temperature, then they are softened and the moisture content is increased and homogenized. But when the moisture content is less than FSP (Fibre Saturation Point), the impact has been an observable decrease in tensile index. It is thought that greenwood makes better pulp than dry wood, thus an online moisture measurement would help avoid having a chip moisture content less than the FSP. There are many non-contact moisture measurement technologies. The common problem with sensors of this kind of is that their calibrations depend on the wood species. Furthermore, since such sensors actually measure chip surface moisture, the average moisture content of wood chips cannot be obtained directly. A generally known method used to overcome this problem consists of calibrating the sensor with an oven-dry moisture content of the chips. This method considered the difference of moisture between the surface and center of wood chip as a constant. For frozen chips, the distribution of moisture content in chips can be regarded as uniform, then the surface moisture content can be regarded as an average moisture content, so this method can be applied. But for unfrozen chips, the distribution of moisture in the chips is influenced by chip ambient air conditions such as air temperature, velocity and relative humidity as well as chip temperature. Any change of these parameters will change the difference of moisture content between the chip surface and center. For this reason, the precision of the average moisture measurement cannot be ensured. To obviate such limitation, the non-contact, moisture sensor provided on the inspection station as described above is preferably used to measure chip surface moisture content for wood chips, along with a phenomenological model allowing to calculate the average moisture content from surface moisture content.

More specifically, chip surface moisture content is estimated using a model based on an experimental moisture measurement and a set of optical parameters representing light reflection characteristics of the wood chips. A position and time dependent model is preferably defined by:

$$M(x,t) = a_1 M_M(x,t) + a_2 H + a_3 S + a_4 L + a_5 K + C \quad (13)$$

wherein:
M(x,t) is the chip surface moisture content (%);
Mm(x,t) is the measured moisture content (%);
H, S, L are color components within chosen color space;
K is chip darkness;
$a_1$ to $a_5$ are predetermined coefficients; and
C is a predetermined constant.

Chip optical properties can be used to adjust the calibration whenever wood species have varied. The experiment demonstrated that calibration adjustment would increase the measuring accuracy from ±5% to ±2% when black spruce contains unknown proportion of balsam fir (0-30%) and jack pine (0-10%). The above model can be solved to find proper values for $a_1$ to $a_5$ and C by known linear regression or PLS methods.

Taking into account the transport phenomena of moisture in wood chip, a phenomenological model is introduced. In pulping process, normally a lower chip moisture that is less than FSP (fibre saturation point) needs more energy and produces pulp quality problem. For this reason, the chip moisture content always overpasses the FSP, but the variation of the chip moisture content exists in chips transport and storage processes. If the relative humidity of air equals 100%, the chip water absorption rate is greater than or equal to evaporation rate, the chips will absorb the water from air in order to reach the equilibrium moisture content, and the distribution of the moisture content tends to be uniform. This condition may be observed in chip pile center. It is worth pointing out that the chip temperature affects chip ageing rate and when the temperature drops to dew point, the condensation occurs. If the relative humidity of air is less than 100%, there are two conditions:

1. Air Temperature>Chips Temperature

This is a chip drying process involving simultaneous, coupled heat and mass transfer phenomena. Heat is transferred from the surrounding air to the chips in order to increase the chip temperature and to evaporate the chip surface moisture, the moisture being transferred as a liquid and/or vapor within a chip and as a vapor on the chip surface. The velocity of air will increase the moisture evaporation rate and heat convection rate etc. If the evaporation rate is less than the movement rate of the chip moisture from the inner to the surface, the surface moisture content is equal to the chip average moisture content, otherwise, the surface moisture content is always less than the average moisture content. In this condition, the condensation may be occurred when the chip temperature is reduced below dew point (i.e. its saturation temperature), which will significantly influence measurement precision of the NIR sensor. If the evaporation rate is greater than and/or equal to the condensation rate, the influence of the condensation can be reduced or eliminated. The evaporation rate is governed by chip and air conditions and especially by air velocity.

2. Air Temperature≦Chips Temperature

This is a special case where the heat and moisture of chips will be transferred from the chips to the surrounding air, the surface moisture content being less than the average moisture content. The moisture movement rate in the chips and evaporation rate on the chip surface decreased with the decrease of the air temperature. A high air velocity may strongly increase the moisture evaporation rate and lightly increase the moisture movement rate in the chips.

Figure 36:
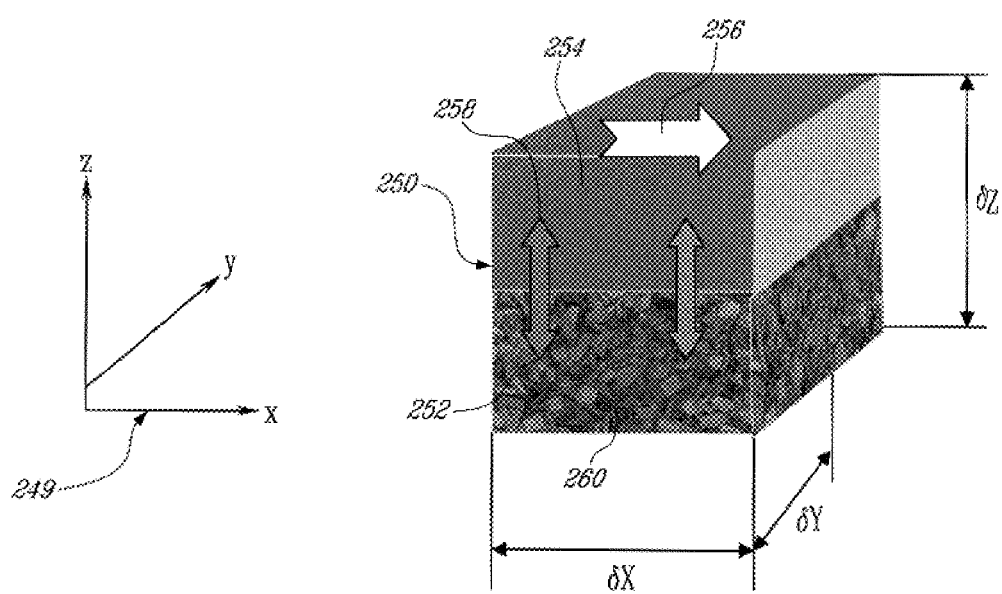
FIG. 36 is a schematic representation of a control volume used for average chip moisture estimation.
Figure 37A:
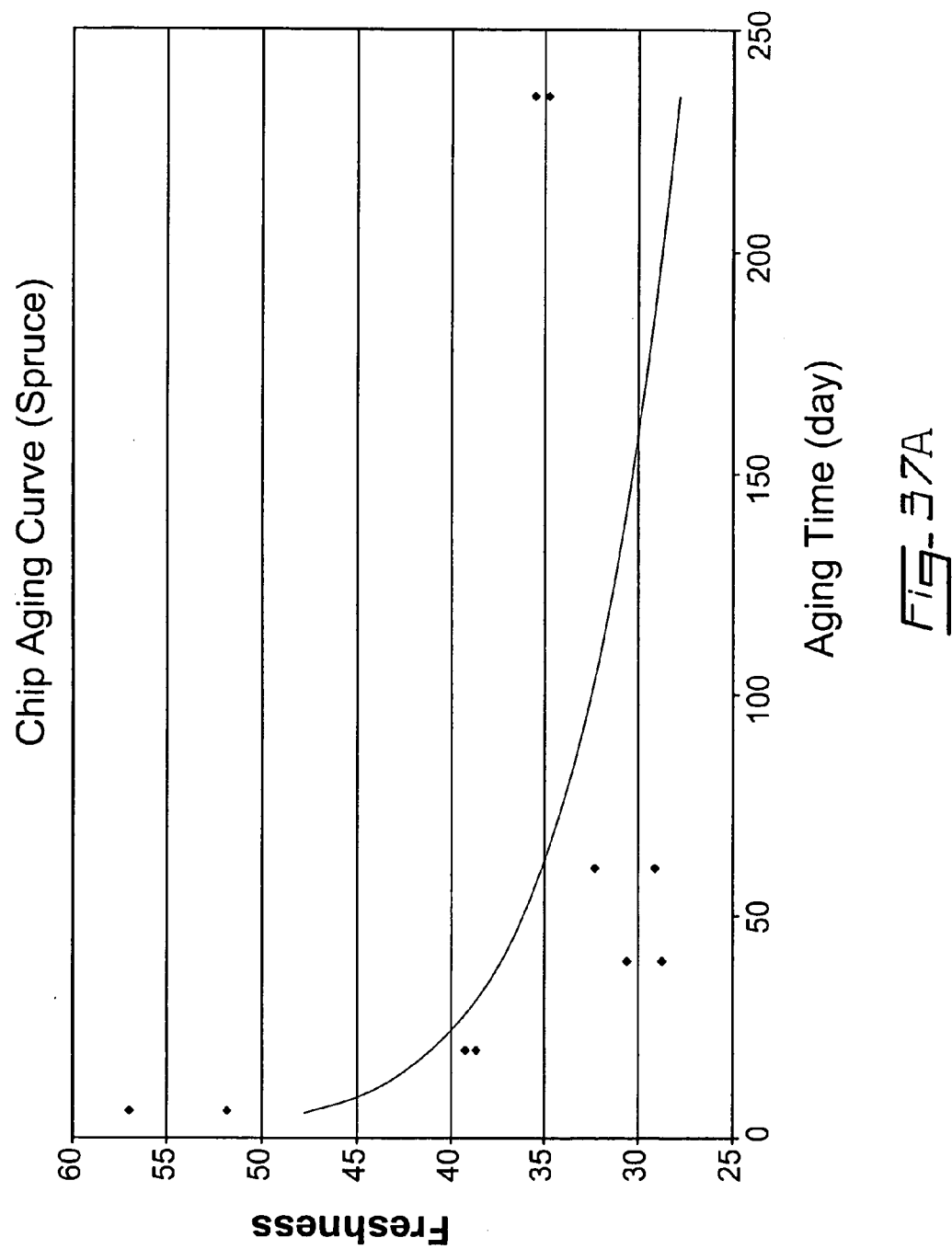
FIGS. 37a to 37d are graphs showing the behavior of wood chips freshness as a function of time for various species.
Figure 37B:
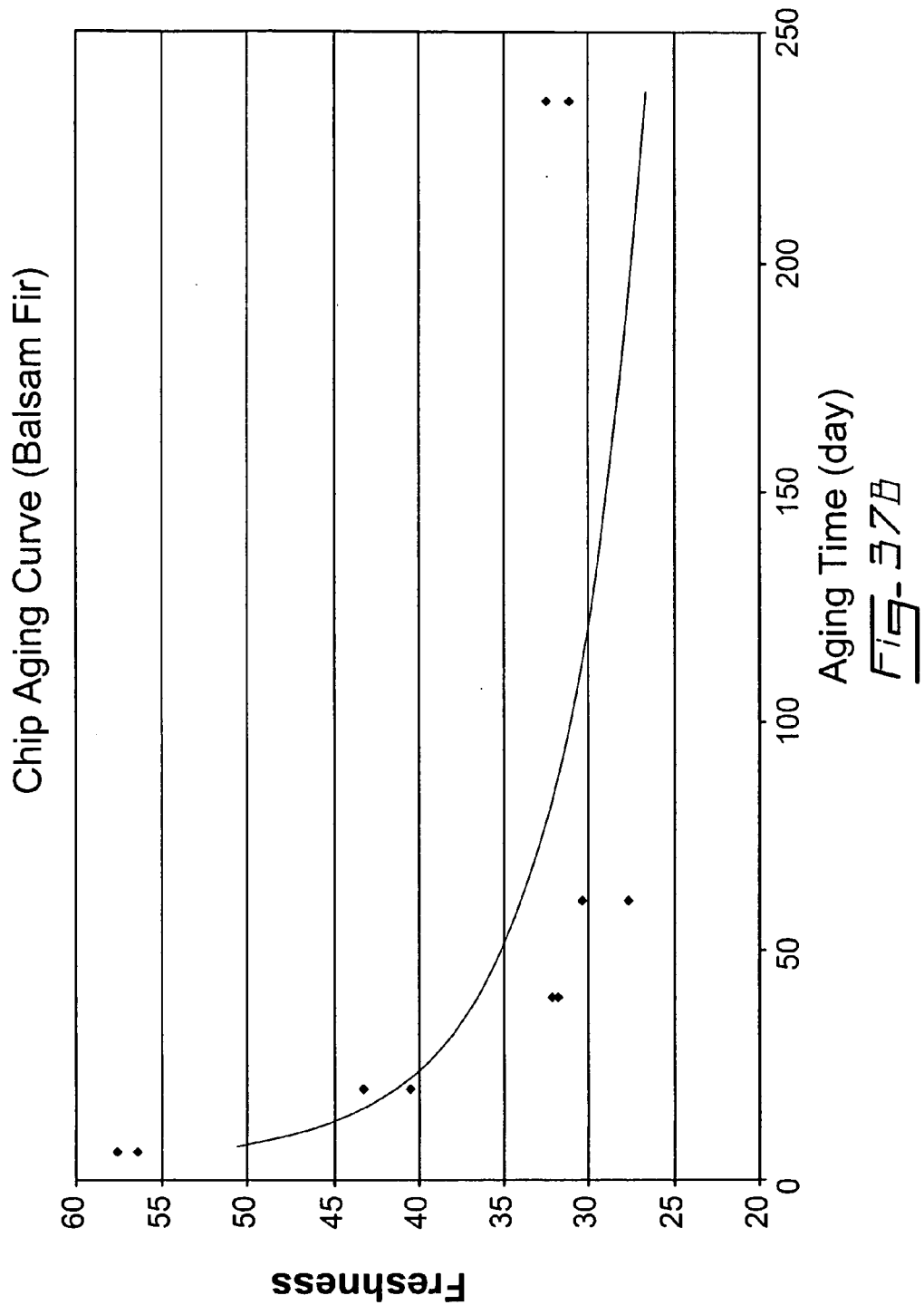
Figure 37C:
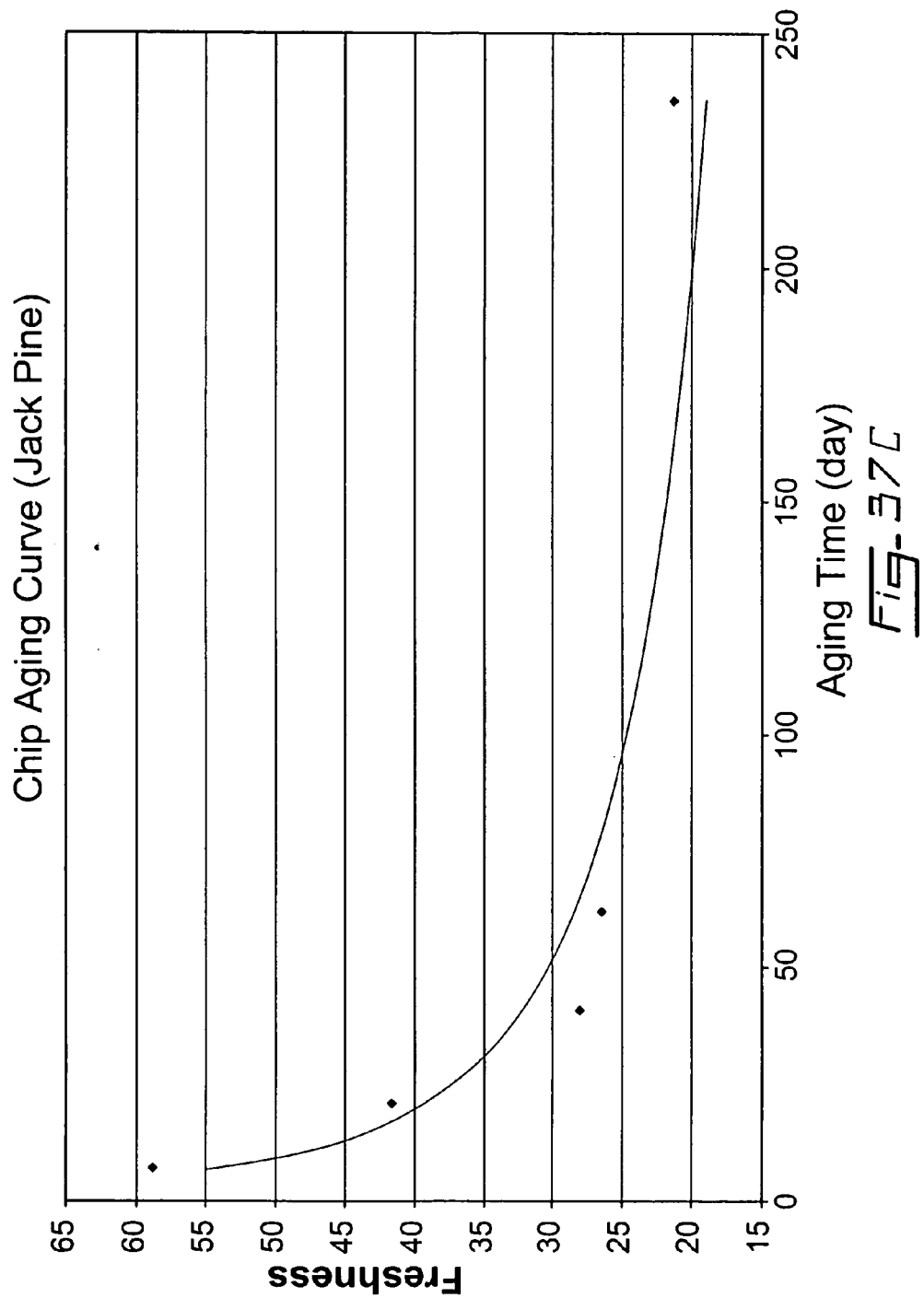
Figure 37D:
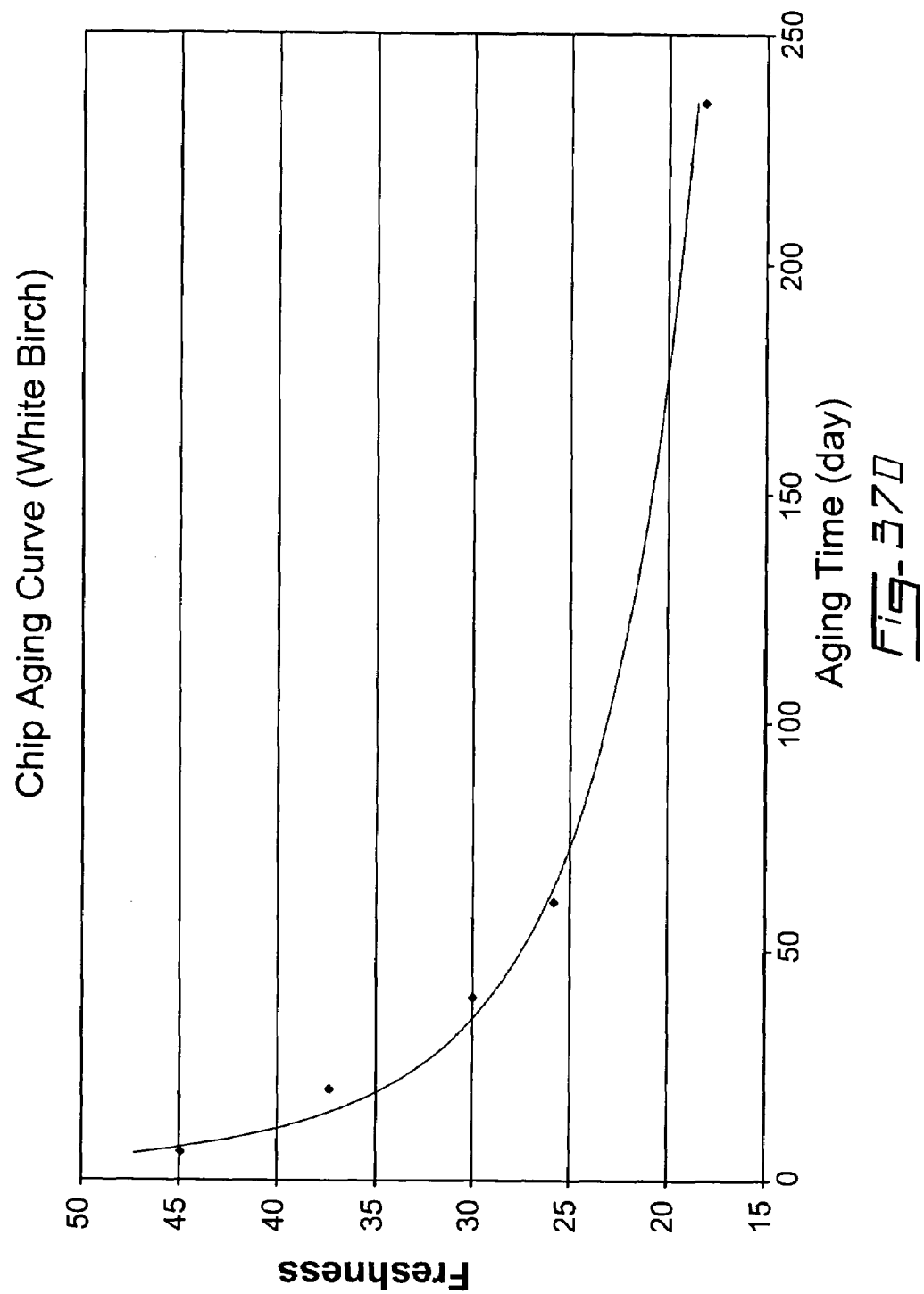

As we have mentioned in the previous section, the mills require chip moisture content to overpass the FSP, thus the moisture that moves in a chip and/or exchanges between the chip and air is free water. Chip is a heterogeneous porous material, the moisture flow in a chip and the water transfer between the chip and air are governed by the driving forces such as: pressure gradient, moisture concentration gradient, capillary pressure, temperature gradient etc. The heat transfer between the chip and air is governed by the driving forces such as: temperature gradient, latent heat, water flow, and pressure gradient, etc. During the wood chips transport by a conveyor, the heat, mass, and momentum are simultaneously transferred across the boundary of the air and wood chips. In order to establish a mathematical model that can correctly describes these phenomena, a control volume is proposed as will be now described in view of FIG. 36. With respect to spatial reference system 249, the control volume generally designated at 250 contains one part of air at 252 and one part of wood chips at 254. The air flow is in x-direction as indicated by arrow 256 and the transfer of the heat and mass is in the z-direction as indicated by arrows 258 and 260, respectively. Supposing that the average moisture content of chips, and the heat and mass transfer in the y-z plane section are identical, then the control volume can be simplified from three-dimensions to one-dimension (x-direction). Thus, an average moisture content of surface layer chips in x-direction can represent the average moisture content of the control volume 250. This hypothesis is appropriate with single infrared moisture sensor measurement, if two or more sensors are installed in the y-direction, the control volume can be simplified to two-dimensions measurement. One more simple method can be applied according to one-dimension model that can be moved in y-direction, thereby one solves the model with different sensor measurements and average the calculated results. According to the proposed approach, the average moisture content is estimated using a model based on transport phenomena relations as a function of time and position in a spatial reference system. These transport phenomena relations include a momentum balance relation expressed by:

$$\frac{\partial}{\partial t}[\rho_a(x,t)v_a(x,t)] = -\frac{\partial}{\partial x}[\rho_a(x,t)v_a^2(x,t)] - \frac{\partial}{\partial x}[P(x,t)] - \frac{\partial}{\partial x}[\tau(x,t)] \quad (14)$$

wherein:

$\tau(x,t)$ is a stress tensor (produced by viscosity, friction, etc.) per unit distance, Pa;

$\rho_a(x,t)$ is air density, Kg/m$^3$;

$v_a(x,t)$ is air velocity, m/s; and $P(x,t)$ is total pressure, Pa.

During chips transport, chip moisture transfer may occur simultaneously with a heat transfer, either as a result of temperature difference between the air and chips or due to absorption or evaporation of moisture for air/chips to chips/air. Therefore, the transport phenomena relations preferably further include heat and mass balance relations. Wood chip being a capillary porous heterogeneous material, extending a Luikov's system of equations of heat and mass transfer, the heat and mass balance relations can be expressed by:

$$\frac{\partial}{\partial t}\left[c_{pb}(x,t)\rho_b(x,t)T_b(x,t) - \rho_w(x,t)\lambda(x,t)M(x,t)\right] = \quad (15)$$

$$\frac{\partial}{\partial x}\left[k_b(x,t)\frac{\partial T_b(x,t)}{\partial x} + \right.$$

$$\left. v_c(x,t)\rho_a(x,t)c_{pa}(x,t)\left[T_{db}(x,t) - T_b(x,t)\right]\right]$$

$$\frac{\partial}{\partial x}\left[D_b(x,t)\frac{\partial M(x,t)}{\partial x} + \frac{D_b(x,t)c_{pb}(x,t)}{\lambda(x,t)}\frac{\partial T_b(x,t)}{\partial x}\right] = \quad (16)$$

$$\frac{\partial}{\partial t}[M(x,t)]$$

wherein:

x is the position along a main direction within the spatial reference system;

t is time;

$C_{pb}(X,t)$ is chip specific heat, J/(Kg.K);

$\rho_b(x,t)$ is green wood density, Kg/m$^3$;

$T_b(x,t)$ is chip temperature, K;

$\rho_w(x,t)$ is chip moisture density, Kg/m$^3$;

$\lambda(x,t)$ is heat of vaporization, J/Kg;

M(x,t) is the chip surface moisture content, %;

$c_{pa}(x,t)$ is air specific heat, J/(Kg.K);

$T_{db}(x,t)$ is dry-bulb temperature, K;

$k_b(x,t)$ is chip thermal conductivity, W/(m.K);

$v_c(x,t)$ is heat convection velocity, m/s; and $D_b(x,t)$ is diffusion coefficient, m$^2$/s.

The chips transport is a continuous chips flow that comes from a silo or pile, passes through air of the refiners or digesters, without any air flow vertically traversing the chips flow. Furthermore, one can assume that the transfer of the temperature and moisture between the chips is realized by the air surrounding the chips. On the basis of these statements, the transport phenomena relations can be associated with initial and boundary conditions expressed by:

$$T_b(x,0) = T_p \quad (17)$$

$$M(x,0) = M_0 \quad (18)$$

$$\left.\frac{\partial T_b(0,t)}{\partial x}\right|_{x=0} = 0; \text{ and } \left.\frac{\partial T_b(l,t)}{\partial x}\right|_{x=l} = 0 \quad (19)$$

$$\left.\frac{\partial M(0,t)}{\partial x}\right|_{x=0} = 0; \text{ and } \left.\frac{\partial M(l,t)}{\partial x}\right|_{x=l} = 0 \quad (20)$$

wherein $T_p$ is initial chip temperature;

$M_0$ is initial chip surface moisture content; and l is transport distance.

The model parameters are functions of the state variables of the system, the state variables can be regarded as air temperature, relative humidity, velocity, chip temperature etc. Solving the system of equations (14) to (20) using numerical known techniques, the average moisture content of the chips is obtained.

Figure 38:
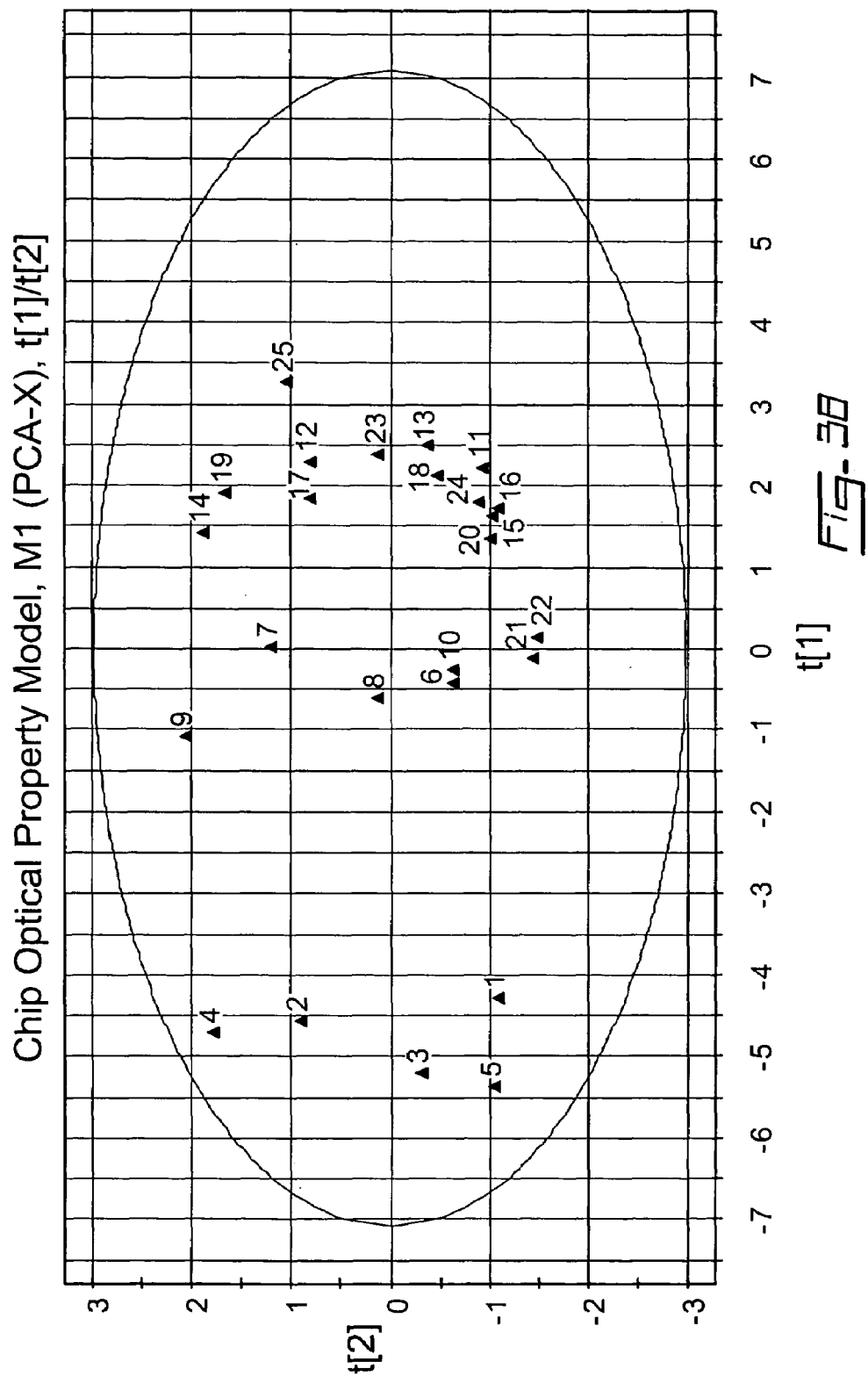
FIG. 38 is a typical PCA score plot according to a chip optical property model.
Figure 39:
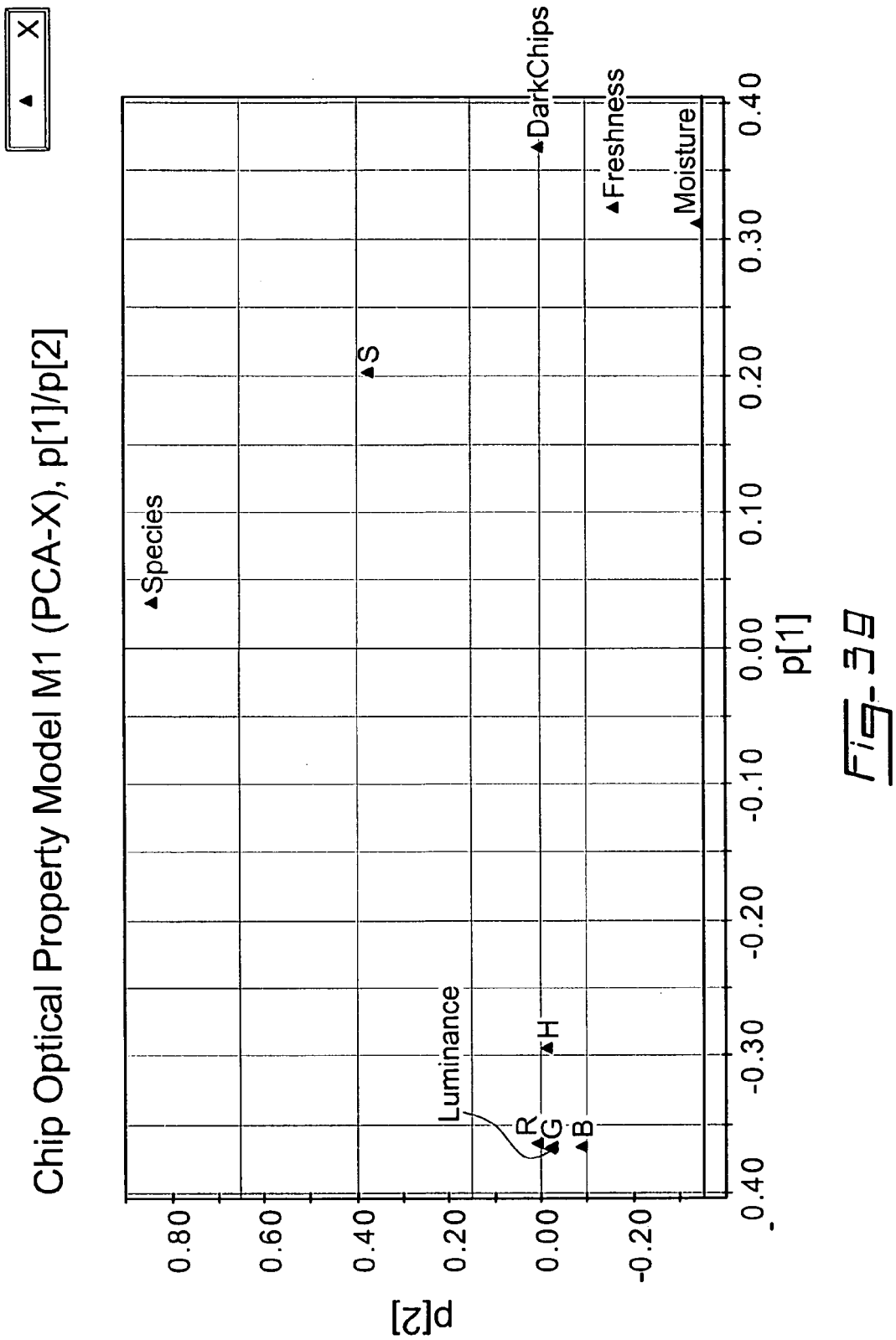
FIG. 39 is a PCA loading plot corresponding to the score plot of FIG. 38.

Since it has been found that chip optical parameters correlate with chip ageing and species information, it is proposed to model these properties. The behavior of wood chips freshness as a function of time is illustrated in FIGS. 37*a* to 37*d* for various species, namely spruce, balsam fir, jack pine and white birch. Working from measurement trials referred to above, in which chip freshness (ageing), and species are controlled, a FFNN (Feedforward Neural Networks) model is constructed. FFNN are known to have an empirically demonstrated ability to approximate complex functions. They are defined by the way they work and the way they are trained. The selection of useful input variables for the FFNN has been performed using known PCA (Principal Component Analysis) technique from the trials results, for the purpose of wood chip quality modeling. PCA has proved to be useful to characterize the test results considering two principal components, even if the model can have more than two principal components. Referring to FIG. 38 showing a typical PCA score plot for a chip optical property model, it can be seen that tests 1-5 form a group, tests 6-10 and 21-22 form a second group, the remaining tests forming a third group. These groups are found to represents different chip freshness (aging) states. Turning now to FIG. 39 showing a corresponding PCA loading plot, it can be seen that optical parameters R, G, B and Luminance are correlated (Luminance and G actually match), that the Freshness Grade share similar information with the moisture, dark chip content (D), R, G, B, H and Luminance. The Species Grade share similar information with S and moisture. Using PCA model we can determine the most important measurement parameters contributing to the prediction of the quality model.

Figure 40:
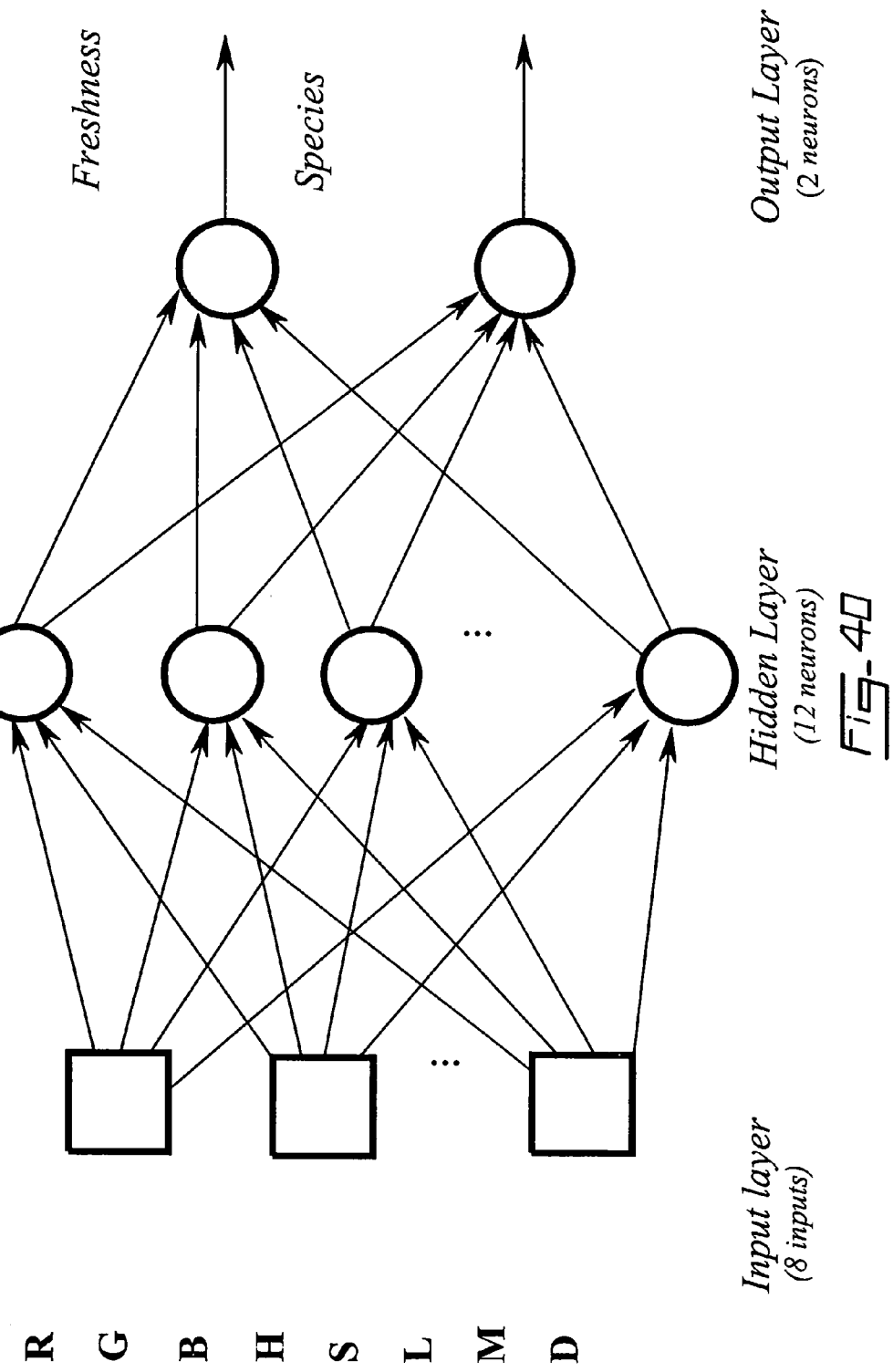
FIG. 40 is an exemplary FFNN model to estimate freshness and species information.

The exemplary FFNN model shown in FIG. 40 is constructed to have 8 inputs, one hidden layer with 12 neurons, and one output layer with 2 neurons. In the hidden layer, a log-sigmoid transfer function was used, and in the output layer a linear transfer function was used in order to obtain a broad range of grades [1, 10]. The well known Levenberg-Marquardt algorithm was used to train the model. The inputs are R, G, B, H, S, L, M, and D, while the outputs are the grades of freshness and species composition or the purity of a main species forming a chip sample. As to freshness modeling, the ageing grade is used instead of the ageing time, since the chip ageing state not only depends on time but also on environmental conditions. According to the above mentioned trials, the freshness of groups A, B, C, D are defined as grade 1, 4, 7, 8, respectively, while groups E and F are defined as grade 10. On the basis of the trials, 100% black spruce is defined as grade 1, 60% spruce with 40% jack pine is defined as grade 2, 60% spruce with 40% white birch is defined as grade 3, and 20% spruce with 40% jack pine and 40% white birch is defined as grade 4. An example of chip qualitative freshness and species simulation result is illustrated in Table 5 referring to such grade definition.

TABLE 5

| Chip properties online measurements | | | | | | | | Qualitative grade | |
|---|---|---|---|---|---|---|---|---|---|
| D | R | G | B | H | S | L | M | Freshness | Species |
| 25 | 72 | 52 | 31 | 22 | 103 | 51 | 55% | 1 | 1 |
| 89 | 40 | 27 | 14 | 21 | 122 | 27 | 71% | 6.8 | 2 |
| 52 | 60 | 41 | 21 | 21 | 124 | 41 | 60% | 4.5 | 3 |
| 93 | 33 | 22 | 13 | 20 | 112 | 23 | 61% | 10 | 4 |

This model was trained using laboratory test results. For application in mills, the qualitative grade may be defined according to each mill's real conditions and measurements. The measured input-output must be registered in a database in order to prepare the training patterns.

As to chip size distribution qualitative modeling, the quality of chips satisfying the criteria of Table 2 may be different because of variations in the size distribution. For example, when 100% of the chips are 15.9-22.2 (mm) in size, they can be considered as grade 1. 1% of fines, with 15% of 4.8-9.5 (mm), with 25% of 9.5-15.9 (mm), with 50% of 15.9-22.2 (mm), with 9% of oversize can be defined as grade 10. The other combinations may be regarded as grades 2-9, according to the following training example. The training file has to contain all possible of different chip size combination in admissible range. The importance of each combination must be defined by both mathematic and real process condition. Table 1 is an example of chip quality criteria (admissible range), the size in the interval [15.9, 22.2] mm is preferable, and the oversize, small size, and fines must be restricted. Taking into account the condition mentioned above, one part of the training file for define the quantitative quality of woodchip size is listed in Table 6.

TABLE 6

| Quantitative grade | >28.6 mm | 15.9-22.2 mm | 9.5-15.9 mm | 4.8-9.5 mm | <4.8 mm |
|---|---|---|---|---|---|
| 1 | 0 | 100 | 0 | 0 | 0 |
| 2 | 2 | 93.89 | 3 | 1 | 0.11 |
| 3 | 2 | 88.5 | 6.28 | 3 | 0.22 |
| 4 | 4 | 83.67 | 8 | 4 | 0.33 |
| 5 | 7 | 75.56 | 11 | 6 | 0.44 |
| 6 | 8 | 69.46 | 14 | 8 | 0.54 |
| 7 | 10 | 63 | 16.33 | 10 | 0.67 |
| 8 | 12 | 58 | 18.22 | 11 | 0.78 |
| 9 | 13 | 53 | 20.11 | 13 | 0.89 |
| 10 | 15 | 50 | 19 | 15 | 1 |

Figure 41:
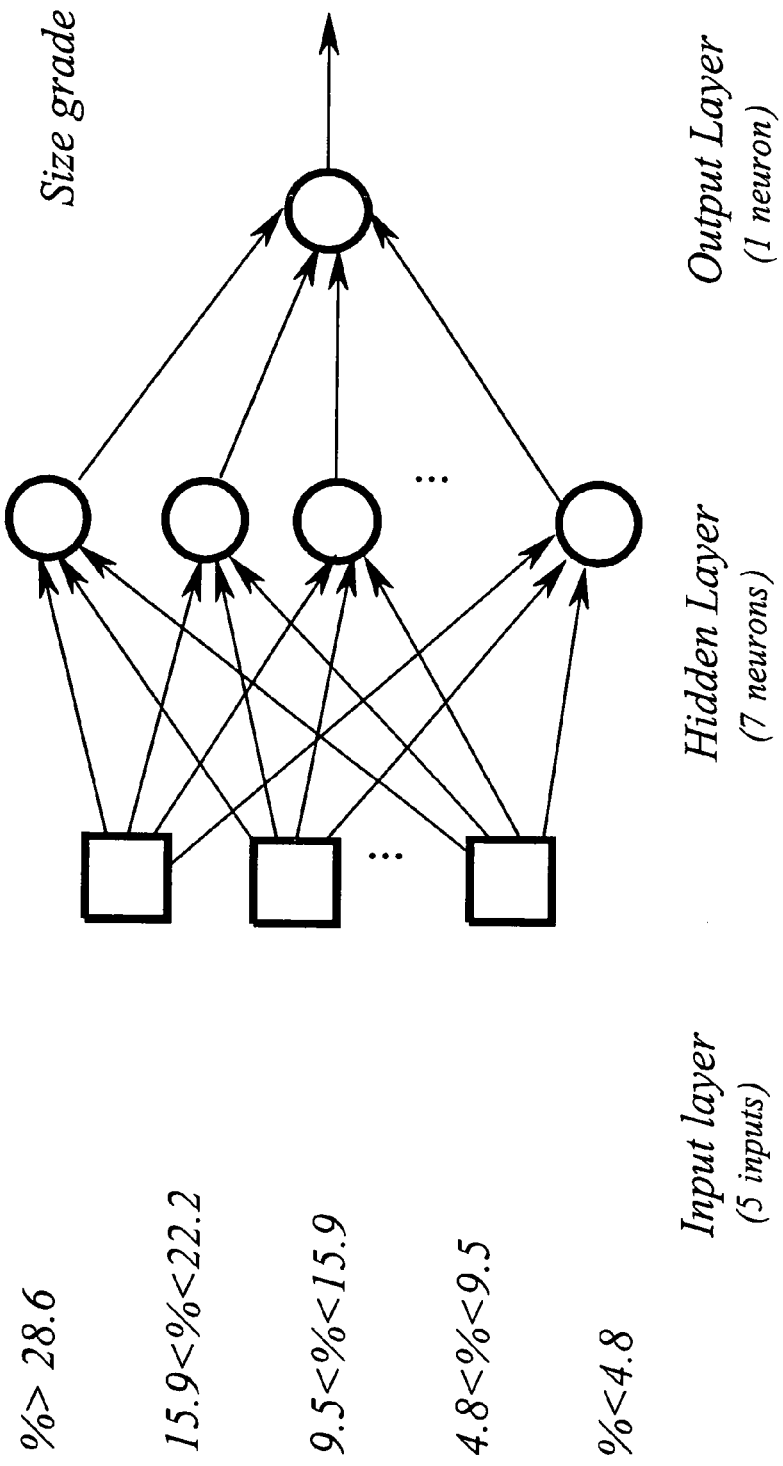
FIG. 41 is an exemplary FFNN model to estimate chip size distribution.

An FFNN quantitative model constructed for size grade estimation is shown in FIG. 41. This model has 5 inputs, 1 hidden layer with 7 neurons, and 1 output layer with 1 neuron. In the hidden layer, a log-sigmoid transfer function was also used, and in the output layer, linear transfer function was used in order to obtain a wide grade range [1, 10]. The Levenberg-Marquardt algorithm was also used to train the model. An example of chip qualitative size distribution simulation result is illustrated in Table 7 referring to such grade definition.

TABLE 7

| >28.6 | 15.9-22.2 | 9.5-15.9 | 4.8-9.5 | <4.8 | Size grade |
|---|---|---|---|---|---|
| 0 | 100 | 0 | 0 | 0 | 1 |
| 8.33 | 72.22 | 13.89 | 8.33 | 0.44 | 5.8 |
| 13.33 | 55.56 | 22.22 | 13.33 | 0.56 | 8.4 |
| 9 | 50 | 25 | 15 | 1 | 10 |

If the mill has special requirements regarding chip distribution, a training file can be reoriented. The advantage of this model is to use a qualitative value to evaluate the chip distribution grade.

As to bark and moisture content qualitative values, they can be measured directly as explained above, and the definition of qualitative grades is listed in Table 8.

TABLE 8

| | Qualitative Grade | | | | | | | | | |
|---|---|---|---|---|---|---|---|---|---|---|
| % | 1 | 2 | 3 | 4 | 5 | 6 | 7 | 8 | 9 | 10 |
| B | 0 | 0.1 | 0.2 | 0.3 | 0.4 | 0.5 | 0.6 | 0.7 | 0.8 | ≧1 |
| M | >43 | 41 | 39 | 37 | 35 | 33 | 31 | 29 | 27 | 25≦ |

Impurities were not considered in this simulation since chip washing and screening are carried out for their removal. Even if online measurement method is not employed to detect chips including knots and rot, the proportion of such defects in wood chips being stable since they are natural part of the wood, they can be ignored. In the case of ageing, rot content may increase, thus the chip freshness is also an indicator of rot content. The experience of the mill has shown that these two parameters are not too critical to the TMP process. The definition of chip quality is also representative without them.

As to chip Quality Simulation, it can be simulated using qualitative grade definition and modeling. The weighting factors and simulated parameters according to Tables 5, 6, and 7 are listed in Table 9.

TABLE 9

| | Freshness | Species | Size | Bark | Moisture |
|---|---|---|---|---|---|
| Weighting | 0.15 | 0.2 | 0.4 | 0.2 | 0.05 |
| Grade | 4.5 | 3 | 5.8 | 9 | 2 |

As shown in Table 9, for the considered example, chip size distribution is the most significant parameter, while moisture is the least significant. Using equation (3), a chip quality grade Q=5.5 is obtained.

Normally, a mill pays chip suppliers when the chips satisfy the "Chip Quality Criteria" listed in Table 1. Using chip quality, the online sensor can measure a large quantity of chips, thus making for a representative sample. The mill pays the supplier according to different quality grades, which makes more sense.

In chip receiving areas, chips are unloaded onto a pile or into a silo immediately after sampling. Using the online measurement, chips can be refused or accepted before they are unloaded from the truck. They can also be sent to a related pile or silo, where they will be combined with chips of a similar quality.

Chip quality online measurement is very useful for stabilizing chip input. Feedback information will control chip-feeding screws so as to take suitable proportions of chips from different piles or silos.

Using PLS (Projections to Latent Structures) models, pulp quality can be predicted using online chip physical property measurement. Thus, online measured chip quality can also predict pulp quality.

Figure 42:
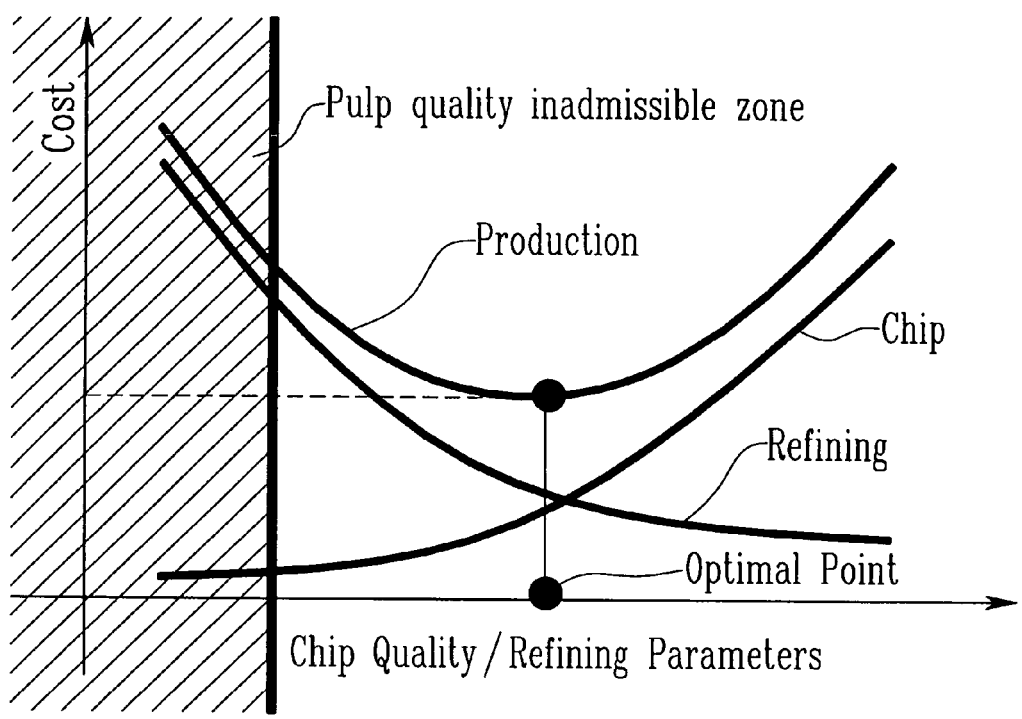
FIG. 42 is a graph representing cost versus chip quality/refining parameters.

As shown in FIG. 42 representing cost versus chip quality/refining parameters, if is supposed that the refining process can be modeled and the pulp quality (target) is given, the refining parameters can be decided using online measured chip quality. It is clear that this measurement is a necessary condition for MPC (Model Predictive Control) of TMP.

For optimal control, the choice of wood chips and refiner control parameters depends on a performance index. As shown in FIG. 7, assuming that the performance index is focused on minimizing the production cost, an optimal chip quality and related refining parameters can be determined. Where chip quality is higher, it is also possible to produce pulp and paper whose qualities correspond to the target, but at an increased cost. For this reason, the online chip quality measurement will help to select optimal quality of chips and to select refiner control parameters.

The invention claimed is:

1. An apparatus for estimating surface moisture content of wood chips comprising:

an infrared surface moisture sensor for generating a chip surface moisture measurement;

image creating means for generating values of a set of optical parameters representing light reflection characteristics of said wood chips; and data processor means for adjusting a calibration of said surface moisture measurement with a model using said parameter values to estimate said surface moisture content.

2. The apparatus according to claim 1, wherein said infrared surface moisture sensor is a near-infrared surface moisture sensor.

3. The apparatus according to claim 2, wherein said optical parameter values include color image pixel data, said image creating means including:

light source means for directing polychromatic light onto an inspected area of said wood chips; and light sensor means for measuring light reflected from said inspected area to generate said color image pixel data representing values of color components within one or more color spaces for pixels forming an image of said inspected area.

4. The apparatus according to claim 3, wherein said model is defined by:

$$M = a_1 M_M + a_2 H + a_3 S + a_4 L + a_5 K + C$$

wherein:

M is said chip surface moisture content;

$M_M$ is said moisture measurement;

H, S, L are said color components within one said color space;

K is chip darkness;

$a_1$ to $a_5$ predetermined coefficients; and

C is a predetermined constant.

* * * * *

UNITED STATES PATENT AND TRADEMARK OFFICE
CERTIFICATE OF CORRECTION

PATENT NO. : 7,292,949 B2
APPLICATION NO. : 10/856883
DATED : November 6, 2007
INVENTOR(S) : Feng Ding It is certified that error appears in the above-identified patent and that said Letters Patent is hereby corrected as shown below:

Column 2
line 46, the number "6,398,914" should read --6,175,092--

Column 7
line 2, the terms "were outdoors" should read --were stored outdoors--

Column 15
lines 19-20, the terms "((heart beat))" should read --«heart beat»--

Column 20 lines 11-14, equation 12 " $p(\mathbf{x}|\omega_i) = \dfrac{1}{\sqrt{2\pi|k_i\Sigma_i|}} \exp\left(-\tfrac{1}{2}(\mathbf{x}-\boldsymbol{\mu}_i)^T (l_o\Sigma_i)^{-1}(\mathbf{x}-\boldsymbol{\mu}_i)\right)$ " should read -- $p(\mathbf{x}|\omega_i) = \dfrac{1}{\sqrt{2\pi|k_i\Sigma_i|}} \exp\left(-\tfrac{1}{2}(\mathbf{x}-\boldsymbol{\mu}_i)^T (k_i\Sigma_i)^{-1}(\mathbf{x}-\boldsymbol{\mu}_i)\right)$ -- line 46, the symbol ".$_1$" should read --$\omega_1$-- line 49, the symbol "U$_{\omega1}$, U$_{\omega2}$, U$_{\omega3}$" should read --u$_{\omega1}$, u$_{\omega2}$, u$_{\omega3}$--

Column 23
line 22, the expression "M$_m$(x,t)" should read --M$_M$(x,t)--

Signed and Sealed this

Sixth Day of April, 2010

David J. Kappos
*Director of the United States Patent and Trademark Office*